(12) United States Patent
Otrando et al.

(10) Patent No.: US 11,844,536 B2
(45) Date of Patent: Dec. 19, 2023

(54) METHODS, SYSTEMS, AND DEVICES FOR INSTABILITY REPAIR

(71) Applicant: Medos International Sarl, Le Locle (CH)

(72) Inventors: Brian Otrando, Cumberland, RI (US); Stephen J. Orphanos, Bridgewater, MA (US); Kirsten H. Aarsvold, Quincy, MA (US)

(73) Assignee: Medos International Sarl, Le Locle (CH)

( * ) Notice: Subject to any disclaimer, the term of this patent is extended or adjusted under 35 U.S.C. 154(b) by 360 days.

(21) Appl. No.: 17/062,200

(22) Filed: Oct. 2, 2020

(65) Prior Publication Data
US 2021/0022754 A1    Jan. 28, 2021

Related U.S. Application Data

(62) Division of application No. 15/913,340, filed on Mar. 6, 2018, now Pat. No. 10,820,915.

(51) Int. Cl.
*A61B 17/17* (2006.01)
*A61F 2/08* (2006.01)
(Continued)

(52) U.S. Cl.
CPC ...... *A61B 17/1714* (2013.01); *A61B 17/0401* (2013.01); *A61B 17/06166* (2013.01); *A61B 17/1615* (2013.01); *A61B 17/1617* (2013.01); *A61B 17/1626* (2013.01); *A61B 17/1633* (2013.01); *A61F 2/0805* (2013.01); *A61F 2/0811* (2013.01); *A61B 17/06061* (2013.01);
(Continued)

(58) Field of Classification Search
CPC . A61B 17/8891; A61B 17/8894; A61B 17/04; A61B 17/14; A61B 16/1615; A61B 16/1633; A61F 2/0805–2002/0888
See application file for complete search history.

(56) References Cited

U.S. PATENT DOCUMENTS 4,421,112 A * 12/1983 Mains ................ A61B 17/1764
606/88
4,927,421 A *  5/1990 Goble ................... A61F 2/0811
606/232

(Continued)

FOREIGN PATENT DOCUMENTS

| CN | 105662503 A | 6/2016 |
| CN | 107440751 A | 12/2017 |

(Continued)

OTHER PUBLICATIONS

Extended European Search Report for EP App. No. 19160829.8 dated Jul. 29, 2019.

*Primary Examiner* — Zade Coley

(57) ABSTRACT

Various exemplary methods, systems, and devices for instability repair are provided. In general, a surgical device can be configured to drill a hole in bone and to deliver a suture anchor into the hole. In this way, a single surgical device can drill the hole and deliver the anchor into the hole for securing soft tissue to the bone. The anchor can be configured to allow the soft tissue to be secured to the bone using a suture coupled to a suture anchor without the need to knot or otherwise tie the suture to secure the soft tissue in place relative to the bone.

19 Claims, 17 Drawing Sheets

(51) Int. Cl.
*A61B 17/04* (2006.01)
*A61B 17/16* (2006.01)
*A61B 17/06* (2006.01)
A61B 17/00 (2006.01)
A61B 90/00 (2016.01)

(52) U.S. Cl.
CPC ............. *A61B 2017/00353* (2013.01); *A61B 2017/00358* (2013.01); *A61B 2017/00477* (2013.01); *A61B 2017/0409* (2013.01); *A61B 2017/0427* (2013.01); *A61B 2017/0438* (2013.01); *A61B 2017/0445* (2013.01); *A61B 2090/0811* (2016.02); *A61F 2002/0841* (2013.01); *A61F 2002/0888* (2013.01)

(56) References Cited

U.S. PATENT DOCUMENTS

| | | | |
|---|---|---|---|
| 5,320,115 A | 6/1994 | Kenna | |
| 5,370,662 A | 12/1994 | Stone et al. | |
| 5,532,223 A | 7/1996 | Jamas et al. | |
| 5,618,314 A | 4/1997 | Harwin et al. | |
| 5,690,676 A | 11/1997 | DiPoto et al. | |
| 6,096,060 A | 8/2000 | Fitts et al. | |
| 6,112,623 A * | 9/2000 | Bigand | A61B 17/8891 81/59.1 |
| 6,146,407 A | 11/2000 | Krebs | |
| 6,206,886 B1 | 3/2001 | Bennett | |
| 6,319,252 B1 | 11/2001 | McDevitt et al. | |
| 6,527,794 B1 | 3/2003 | McDevitt et al. | |
| 6,544,281 B2 | 4/2003 | ElAttrache et al. | |
| 6,641,597 B2 | 11/2003 | Burkhart et al. | |
| 6,673,094 B1 * | 1/2004 | McDevitt | A61B 17/0401 606/232 |
| 6,770,073 B2 * | 8/2004 | McDevitt | A61F 2/0811 606/60 |
| 6,773,506 B2 | 8/2004 | Nakamura et al. | |
| 6,923,813 B2 * | 8/2005 | Phillips | A61B 17/8855 606/86 R |
| 7,329,272 B2 | 2/2008 | Burkhart et al. | |
| 7,618,462 B2 * | 11/2009 | Ek | A61F 2/4657 623/20.14 |
| 7,867,264 B2 * | 1/2011 | McDevitt | A61F 2/0805 606/301 |
| 7,896,907 B2 | 3/2011 | McDevitt et al. | |
| 7,993,369 B2 | 8/2011 | Dreyfuss | |
| 8,012,174 B2 | 9/2011 | ElAttrache et al. | |
| 8,114,128 B2 | 2/2012 | Cauldwell et al. | |
| 8,430,909 B2 | 4/2013 | Dreyfuss | |
| 8,663,279 B2 | 3/2014 | Burkhart et al. | |
| 8,709,013 B2 | 4/2014 | Lombardo | |
| 8,834,543 B2 | 9/2014 | McDevitt et al. | |
| 9,005,246 B2 | 4/2015 | Burkhart et al. | |
| 9,113,859 B2 | 8/2015 | Dooney, Jr. et al. | |
| 9,113,916 B2 | 8/2015 | Lozier et al. | |
| 9,138,220 B2 | 9/2015 | Hernandez | |
| 9,179,907 B2 | 11/2015 | ElAttrache et al. | |
| 9,241,705 B2 * | 1/2016 | Lanois | A61B 17/0401 |
| 9,277,910 B2 | 3/2016 | Nason et al. | |
| 9,289,203 B2 | 3/2016 | Brown et al. | |
| 9,295,460 B2 | 3/2016 | Hoof et al. | |
| 9,526,492 B2 | 12/2016 | Lombardo et al. | |
| 9,526,494 B1 | 12/2016 | Lanois et al. | |
| 9,566,060 B2 * | 2/2017 | Dougherty | A61B 17/0401 |
| 10,820,915 B2 | 11/2020 | Otrando et al. | |
| 2004/0015170 A1 * | 1/2004 | Tallarida | A61B 17/888 606/71 |
| 2008/0208253 A1 | 8/2008 | Dreyfuss et al. | |
| 2009/0076544 A1 | 3/2009 | DiMatteo et al. | |
| 2010/0116893 A1 | 5/2010 | Yu et al. | |
| 2010/0204701 A1 * | 8/2010 | Tallarida | A61F 2/30756 606/80 |
| 2012/0022588 A1 | 1/2012 | Berg | |
| 2013/0150885 A1 | 6/2013 | Dreyfuss | |
| 2013/0158597 A1 * | 6/2013 | Hernandez | A61B 17/0401 606/232 |
| 2014/0277129 A1 | 9/2014 | Arai et al. | |
| 2014/0364906 A1 | 12/2014 | Palese et al. | |
| 2015/0196290 A1 * | 7/2015 | Lanois | A61B 17/0401 606/232 |
| 2015/0245901 A1 * | 9/2015 | Dougherty | A61F 2/0805 606/232 |
| 2015/0313586 A1 | 11/2015 | Burkhart et al. | |
| 2015/0374356 A1 | 12/2015 | Hernandez | |
| 2016/0058551 A1 | 3/2016 | ElAttrache et al. | |
| 2016/0095588 A1 | 4/2016 | ElAttrache et al. | |
| 2016/0157852 A1 * | 6/2016 | Dougherty | A61B 17/0483 606/232 |
| 2016/0220242 A1 * | 8/2016 | Dougherty | A61B 17/0401 |
| 2016/0302785 A1 | 10/2016 | Nason et al. | |
| 2016/0317162 A1 | 11/2016 | Dougherty et al. | |
| 2017/0042530 A1 | 2/2017 | Lombardo et al. | |
| 2017/0303907 A1 * | 10/2017 | Sengun | A61B 17/3423 |
| 2019/0274695 A1 | 9/2019 | Otrando et al. | |

FOREIGN PATENT DOCUMENTS

| | | | |
|---|---|---|---|
| JP | 2006516468 A | 7/2006 | |
| JP | 2016511064 A | 4/2016 | |
| WO | WO-2004071307 A2 | 8/2004 | |
| WO | WO-2014158782 A1 | 10/2014 | |
| WO | WO-2017210620 A1 * | 12/2017 | ......... A61B 17/0401 |

* cited by examiner

METHODS, SYSTEMS, AND DEVICES FOR INSTABILITY REPAIR

CROSS REFERENCE TO RELATED APPLICATIONS

This application is a divisional of U.S. patent application Ser. No. 15/913,340, filed on Mar. 6, 2018, and entitled "Methods, Systems, and Devices for Instability Repair," which is hereby incorporated by reference in its entirety.

FIELD

The present disclosure relates generally to methods, systems, and devices for instability repair.

BACKGROUND

The complete or partial detachment of ligaments, tendons, and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Numerous devices are currently available to re-attach soft tissue to bone. Examples of such currently-available devices include screws, staples, suture anchors and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. Then a suture anchor is deployed in the hole using an appropriate tool. This effectively locks the suture to the bone, with the free end(s) of the suture extending out of the bone. The free ends of the suture are passed through or around the soft tissue and are used to tie the soft tissue securely to the bone. Similarly, a knotless suture anchor may be used by first passing the suture through or around the soft tissue, then passing the suture through the suture anchor, and finally securing the construct in the bone hole. Some systems incorporate the use of a cannulated guide where drilling and anchor placement is performed within the cannulated guide.

While current suture anchors are effective in anchoring soft tissue to bone, one drawback with current suture anchors is that it can be difficult to locate the hole drilled in bone after the drill is removed because of the hole's small size and/or because of tissue and/or other matter obscuring visualization of the hole. The surgical procedure is thus delayed as the surgeon attempts to find the hole. Even once the hole is located, it can be difficult to properly angularly align the anchor for delivery into the hole. If the anchor is not delivered into the hole at the proper angle, the anchor can break by being pushed against bone at an improper angle and/or the anchor can damage tissue and/or other matter near the hole by being pushed thereagainst due to the anchor's misalignment with the bone.

Accordingly, there remains a need for improved devices, systems, and methods for instability repair.

SUMMARY

In general, methods, systems, and devices for instability repair are provided.

In one aspect, a surgical system is provided that in one embodiment includes an elongate shaft having an inner lumen, an anchor configured to be implanted in bone, and a drill. The anchor has a passageway extending therethrough. The drill is disposed within the inner lumen of the shaft, is disposed within the passageway of the anchor with a distal tip of the drill located distal to the anchor, and is configured to rotate relative to the shaft and the anchor to allow a hole to be formed in bone. The drill is configured to be removed from the anchor after formation of the hole by the drill sliding proximally within the inner lumen of the shaft and the passageway of the anchor such that the tip of the drill is not located distal to the anchor.

The surgical system can have any number of variations. For example, the drill can be configured to move from an extended position to a retracted position, the drill in the extended position can be disposed within the inner lumen of the shaft, disposed within the passageway of the anchor with the distal tip of the drill located distal to the anchor, and configured to rotate relative to the shaft and the anchor to allow the hole to be formed in bone, and when the drill in the retracted position the anchor and the shaft can be movable distally relative to the drill to insert the anchor in the hole.

In at least some embodiments, the anchor can have a slot therein that is in communication with the passageway, the drill can have a protrusion extending therefrom, and the drill can be configured to move relative to the anchor to align the protrusion with the slot such that the protrusion is slidable within the slot in moving the drill from the extended position to the retracted position. In at least some embodiments, the slot can be formed in an inner surface of the anchor that defines the passageway, the protrusion can abut a distal surface of the anchor when the protrusion and the slot are misaligned, and/or the anchor can have an opening in a sidewall thereof. The opening can be in communication with the passageway, the opening and the protrusion can be misaligned when the protrusion and the slot are misaligned, and the opening and the protrusion can be aligned when the protrusion and the slot are aligned.

In at least some embodiments, the surgical system can include a handle and an alignment mechanism. The handle can be at a proximal end of the shaft and can include a first alignment feature. The alignment mechanism can include a second alignment feature. The alignment mechanism can be configured to move relative to the handle to align the first and second alignment features, and the alignment mechanism can be operatively coupled to the drill such that the movement of the alignment mechanism relative to the handle also moves the drill relative to the handle. The drill can be prevented from moving from the extended position to the retracted position when the first and second alignment features are misaligned, and the drill can be allowed to move from the extended position to the retracted position when the first and second alignment features are aligned. In at least some embodiments, a bias element can be disposed in the handle and be configured to automatically move the drill from the extended position to the retracted position in response to the first and second alignment features becoming aligned, and/or the anchor can have a slot formed therein, the drill can be prevented from moving from the extended position to the retracted position when the slot and protrusion are misaligned, and the drill can be allowed to move from the extended position to the retracted position when the slot and protrusion are aligned.

In at least some embodiments, the surgical system can include a bias element configured to automatically move the drill from the extended position to the retracted position.

For another example, the drill can have a protrusion formed thereon and extending therefrom at a location proximal to the distal tip of the drill, and the protrusion can be configured to form the hole in bone.

For another example, the surgical system can include a drilling tip disposed on the drill distal to the anchor and proximal to the anchor, and the drilling tip can be configured to form the hole in bone, and the drill being configured to be removed from the drilling tip after formation of the hole such that the drilling tip is disposed in the hole distal to the anchor.

For yet another example, the anchor can have an opening formed therein that is in communication with the passageway, the drill can have a protrusion extending therefrom, and the drill can be prevented from sliding proximally within the inner lumen of the shaft and the passageway of the anchor unless the protrusion is aligned with the opening. In at least some embodiments, a bias element can be configured to automatically move the drill from the extended position to the retracted position in response to the protrusion becoming aligned with the opening.

For another example, a suture can be coupled to the anchor and releasably secured to a handle at a proximal end of the shaft.

In another embodiment, a surgical system includes an elongate shaft having a handle at a proximal end thereof, a drill configured to drill a hole in bone, and an anchor disposed on the drill distal to the shaft. The handle includes a first alignment feature. The drill is movably disposed within the shaft. The surgical system also includes an alignment mechanism movably coupled to the handle and operatively coupled to the drill such that movement of the alignment mechanism relative to the handle moves the drill relative to the shaft. The shaft and anchor are configured to move distally as a unit to insert the anchor into the hole. The drill is prevented from moving proximally within the shaft when the alignment mechanism and the alignment feature are misaligned, and the drill is allowed to move proximally within the shaft when the alignment mechanism and the alignment feature are aligned.

The surgical system can vary in any number of ways. For example, the alignment mechanism can include a rotatable knob. For another example, a bias element can be disposed in the handle, and the bias element can be configured to automatically move the drill proximally relative to the shaft in response to the alignment mechanism and the alignment feature becoming aligned. For yet another example, a proximal surface of the anchor can abut a distal surface of the shaft.

In another aspect, a surgical method is provided that in one embodiment includes drilling a hole in bone with a drill disposed in a shaft of a surgical tool. The drill has an anchor thereon at a location proximal to a distal tip of the drill. The method also includes adjusting an alignment mechanism at a proximal end of the shaft until the alignment mechanism aligns with an alignment feature of the handle, thereby causing the drill to move proximally within the shaft. The method also includes advancing the shaft and anchor as a unit relative to the drill to move the anchor distally in the hole.

The method can vary in any number of ways. For example, the handle can have a bias element therein that automatically causes the drill to move proximally within the shaft in response to the alignment mechanism aligning with the alignment feature of the handle. For another example, adjusting the alignment mechanism can cause movement of the drill relative to the anchor, and the alignment mechanism aligning with the alignment feature can indicate that a protrusion extending from the drill is aligned with a slot extending along the anchor within which the protrusion slides proximally during the proximal movement of the drill within the shaft.

BRIEF DESCRIPTION OF DRAWINGS

This invention will be more fully understood from the following detailed description taken in conjunction with the accompanying drawings, in which.

DETAILED DESCRIPTION

Figure 1:
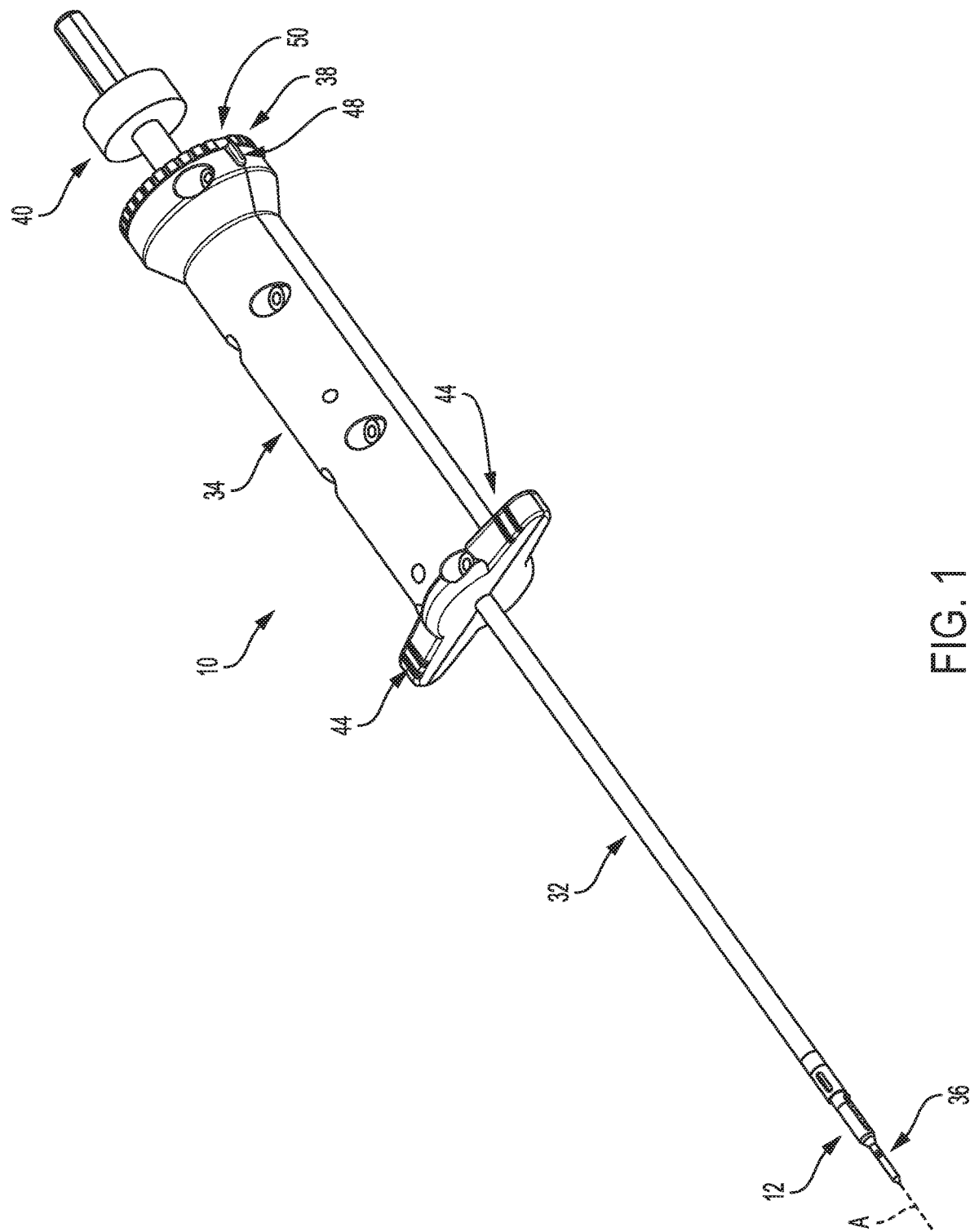
FIG. 1 is a perspective view of one embodiment of a surgical device including a suture anchor coupled thereto.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for instability repair are provided. In general, a surgical device can be configured to drill a hole in bone and to deliver a suture anchor into the hole. In this way, a single surgical device can drill the hole and deliver the anchor into the hole for securing soft tissue to the bone. The anchor can be configured to allow the soft tissue to be secured to the bone using a suture coupled to a suture anchor without the need to knot or otherwise tie the suture to secure the soft tissue in place relative to the bone.

Using the same device for drilling the hole and delivering the anchor into the hole may facilitate delivery of the anchor into the hole at a proper angle, e.g., with a longitudinal axis of the anchor being substantially coaxial with a longitudinal axis of the hole, because the same device is performing the drilling and the delivery. A person skilled in the art will appreciate that the axes may not be precisely coaxial but nevertheless be considered to be substantially coaxial due to any number of factors, such as sensitivity of measurement equipment and manufacturing tolerances for the anchor.

Using the same device for drilling the hole and delivering the anchor into the hole, instead of using one surgical device for the drilling and another surgical device for the anchor delivery, reduces a number of instruments used in the surgical procedure, which may reduce overall cost of the procedure and/or reduce operating room clutter. The surgical device can be configured to remain within the patient's body after drilling the hole such that the anchor can be delivered into the hole without removing the surgical device from the patient's body, which may facilitate the anchor's delivery into the hole at the proper angle since upon the completion of drilling the surgical device can be at a position relative to the hole that properly angularly aligns the anchor with the hole.

Using the same device for drilling of the hole and delivering the anchor into the hole may eliminate the need for a surgeon or other medical personnel to locate the hole before delivering the anchor into the hole, thereby saving time.

In general, the suture anchors discussed herein, also referred to herein as anchors, are configured to be implanted in a body of a patient. The anchors are configured to couple to a suture and to be used in a tissue repair procedure, e.g., an arthroplasty at a joint such as the hip, knee, or shoulder, a meniscal repair procedure for repairing a meniscal tear at a knee, a rotator cuff repair procedure for repairing a torn rotator cuff at a shoulder, etc.

An anchor can be absorbable or non-absorbable. An anchor can be made from any of a variety of materials, e.g., Polyether ether ketone (PEEK), Polylactic acid or polylactide (PLA), BIOCRYL® RAPIDE®, stainless steel, etc. An anchor can be formed by a variety of techniques, for example by an injection molding process such as overmolding or by a post-molding process such as post-molding machining. An anchor can have any of a variety of sizes as appropriate for, e.g., use at a particular anatomical location and with a particular patient.

Figure 2:
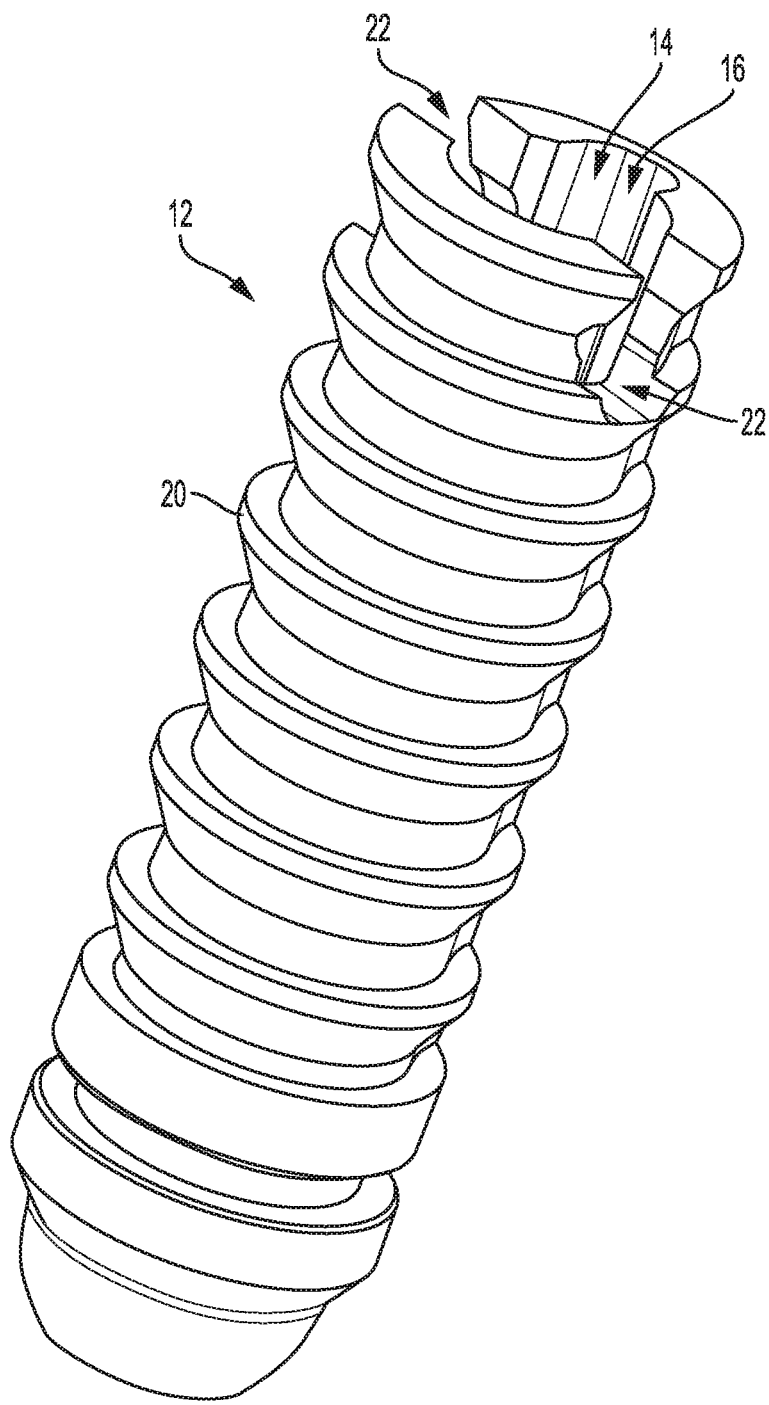
FIG. 2 is a perspective view of the anchor of FIG. 1.
Figure 3:
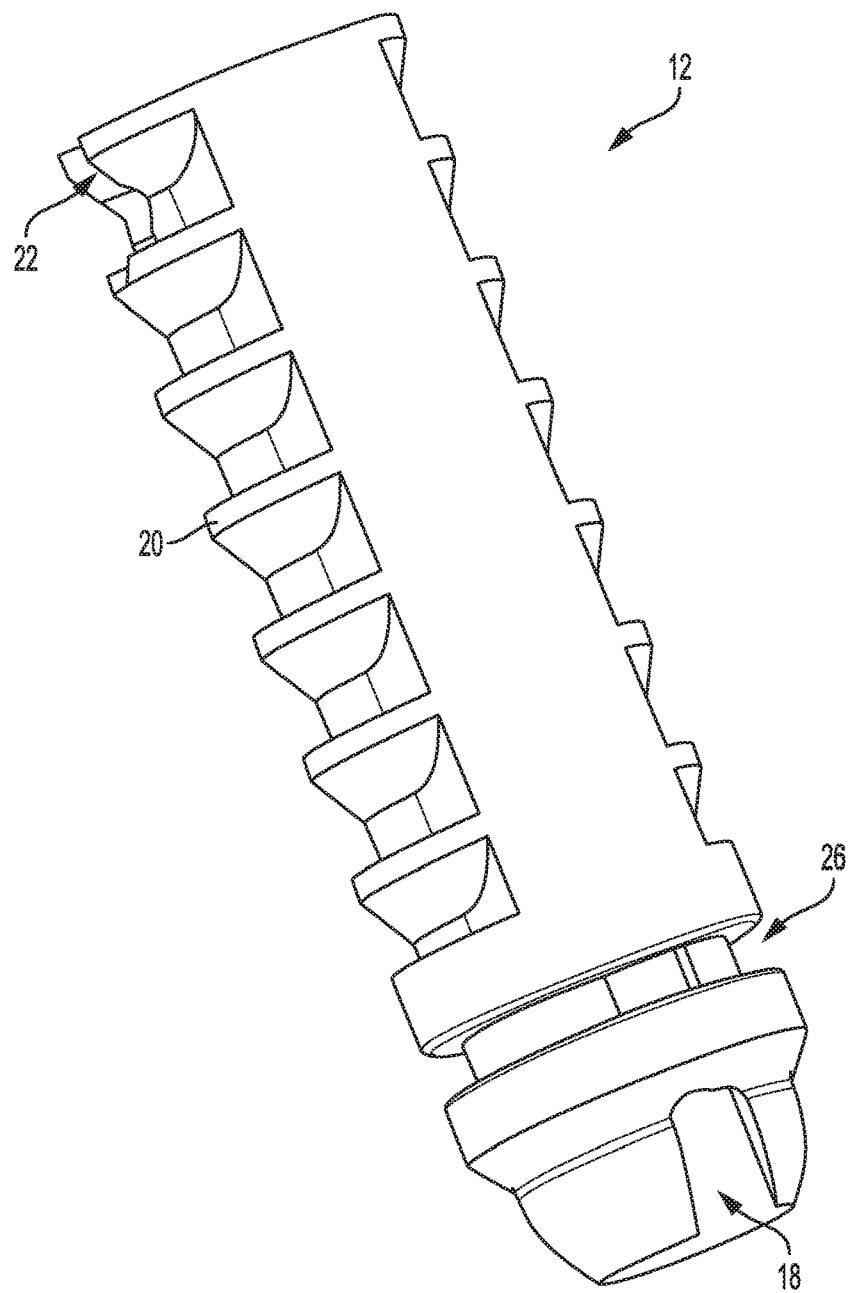
FIG. 3 is another perspective view of the anchor of FIG. 1.

FIG. 1 illustrates one embodiment of a surgical device 10 configured to drill a hole in bone and to deliver a suture anchor 12 into the hole. The anchor 12 is illustrated as a standalone element in FIGS. 2 and 3. The anchor 12 is cannulated and has a passageway 14 extending therethrough. The anchor 12 has a slot 16 that extends longitudinally therealong and that is formed in an internal surface of the anchor 12 that defines the passageway 14. The slot 16 is thus in communication with the passageway 14. The anchor 12 has a keyhole opening 18 formed through a sidewall thereof at a distal end of the anchor 12. The opening 18 is in communication with the slot 16, and hence with the passageway 14, and is located at a distal end of the passageway 14. The anchor 12 has a bone-engaging feature 20 on an exterior surface thereof to help secure the anchor 12 within bone. The bone-engaging feature 20 includes a plurality of barbs in this illustrated embodiment that each extend around a partial circumference of the anchor 12, but the bone-engaging feature 20 can have other configurations. The anchor 12 has an interrupted perimeter at its proximal end due to a pair of opposed openings 22 formed through the anchor's sidewall that extend distally from the anchor's proximal end along a partial longitudinal length of the anchor 12. Various embodiments of suture anchors and bone-engaging features thereof are further described in U.S. Pat. No. 8,114,128 entitled "Cannulated Suture Anchor" issued Feb. 14, 2012, and U.S. Patent No. 2009/0076544 entitled "Dual Thread Cannulated Suture Anchor" filed Sep. 14, 2007, which are hereby incorporated by reference in their entireties.

The anchor 12 has a suture-engaging channel 26 in an exterior thereof that extends circumferentially around an entire perimeter of the anchor 12. The channel 26 is configured to seat a suture therein to attach a suture to the anchor 12 to allow the suture to be anchored in bone with the anchor 12. A suture can be seated in the channel 26 by, for example, being tied around or looped around the anchor 12, molded to the anchor 12, sewn on, etc. The suture being seated in the channel 26 may help protect the suture from being damaged during drilling since the suture is located outside of the drill 36 and anchor 12. The suture seated in the channel 26 can be a tether suture to which one or more operative sutures attached to soft tissue are coupled, e.g., by piercing through the tether suture with a suture passing kite or otherwise, as will be appreciated by a person skilled in the art. The anchor 12 is not shown in FIG. 1 as having a suture attached thereto for clarity of illustration, but a suture would be attached to the anchor 12 and extend proximally therefrom.

Figure 4:
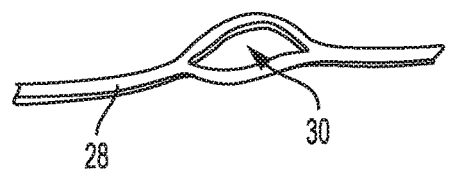
FIG. 4 is a perspective view of one embodiment of a suture.
Figure 5:
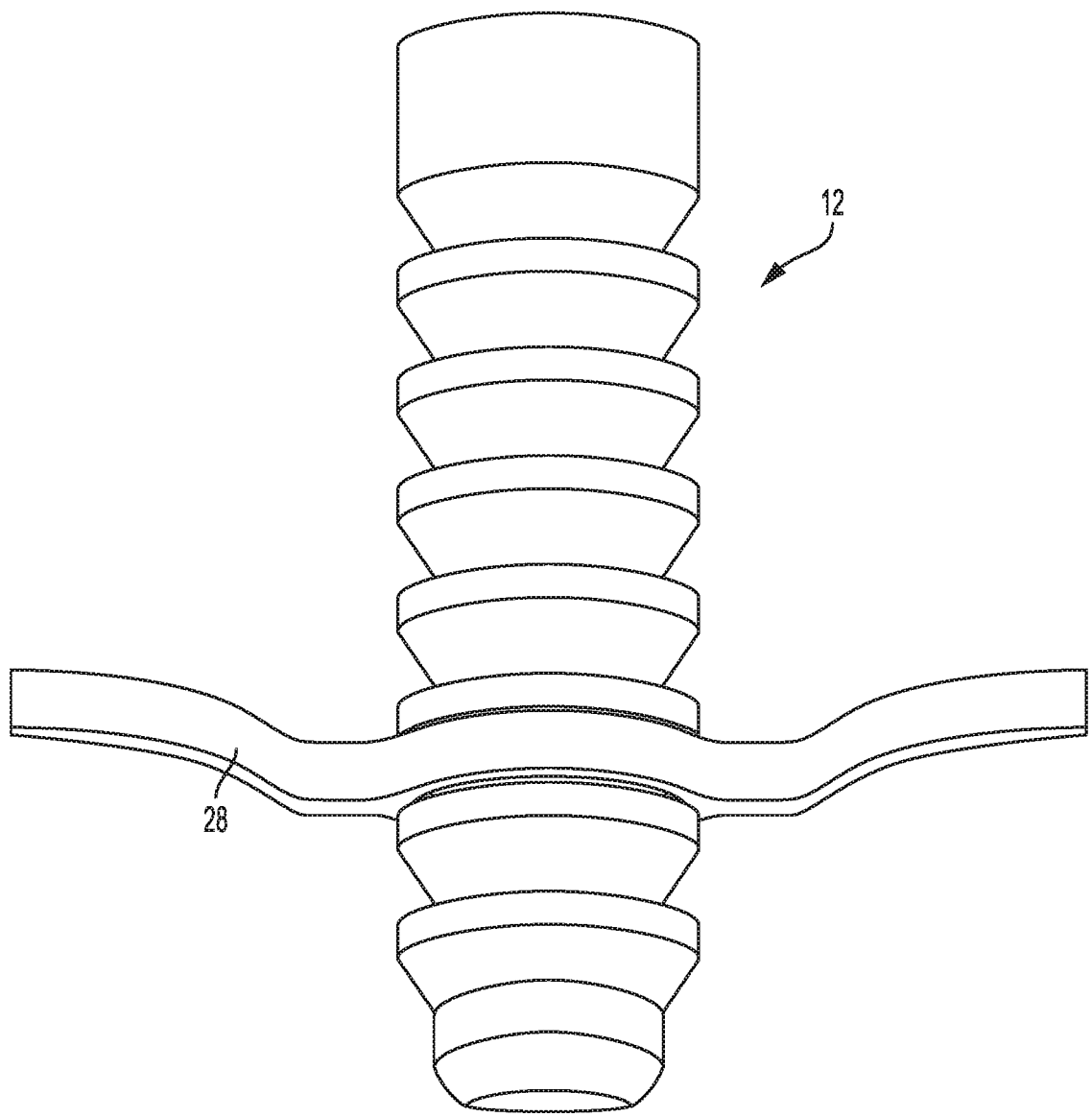
FIG. 5 is a perspective view of the suture of FIG. 4 attached to the anchor of FIG. 1.

In an exemplary embodiment, a suture has a hole formed therein to facilitate seating of the suture within the channel 26. FIG. 4 illustrates one embodiment of a suture 28 having a hole 30 formed therein, e.g., due to bifurcation of the suture 28 at a portion thereof, that can be attached to the anchor 12 and other anchors described herein. The suture 28 is braided in this illustrated embodiment, which may facilitate bifurcation of the suture 28 to form the hole 30. The anchor 12 can be disposed within the hole 30 such that the portion of the suture 28 that defines the perimeter of the hole 30 is seated in the channel 26, as shown in FIG. 5. The suture 28 is flexible, which may facilitate positioning of the suture 28 within the channel 26. A kite or other suture passing instrument can be used to facilitate attachment of the suture 28 to the anchor 12. The suture 28 is flat in this illustrated embodiment but could instead be round.

Figure 6:
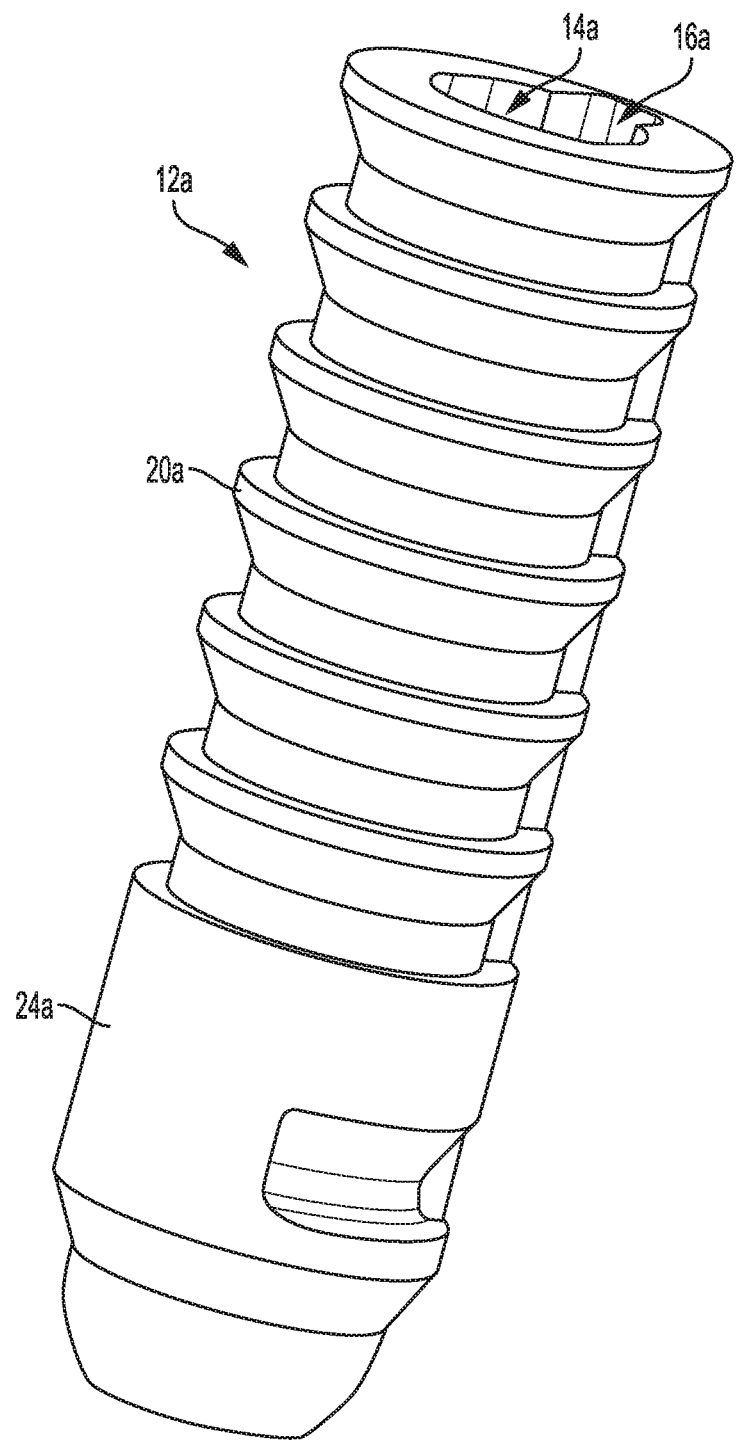
FIG. 6 is a perspective view of another embodiment of a suture anchor.
Figure 7:
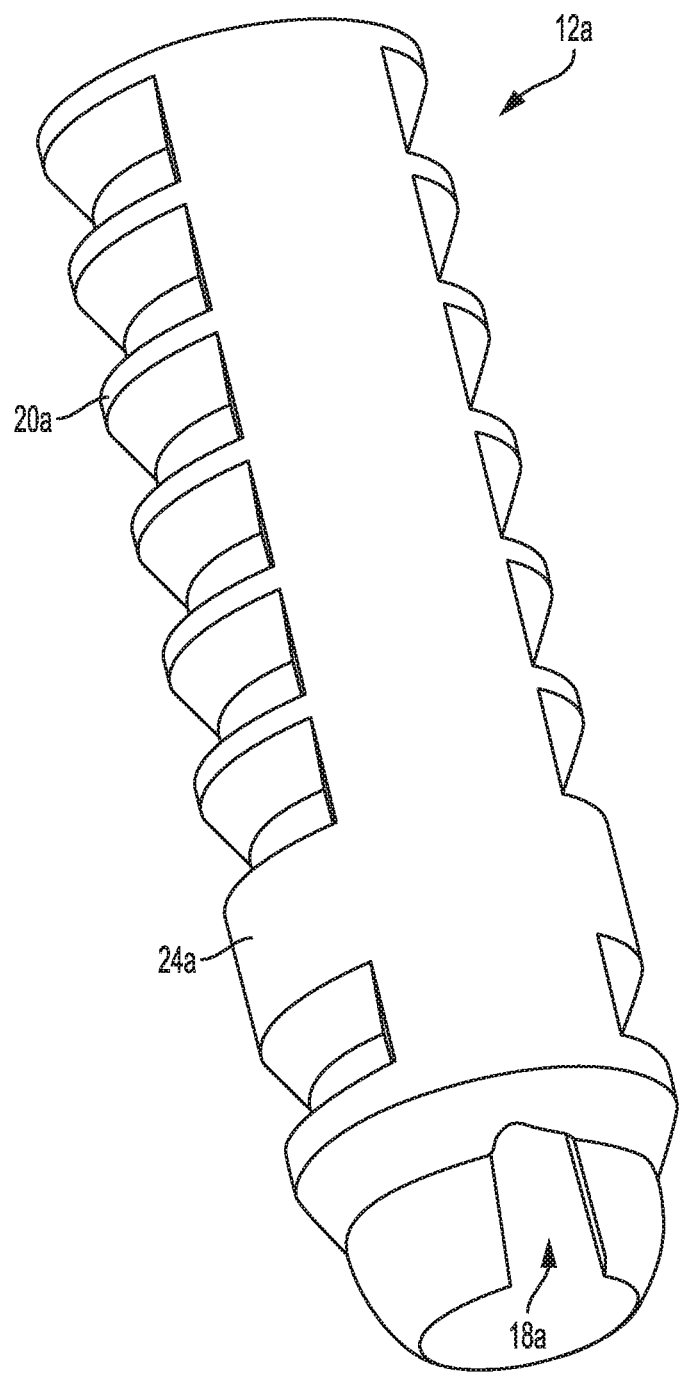
FIG. 7 is another perspective view of the anchor of FIG. 6.
Figure 8:
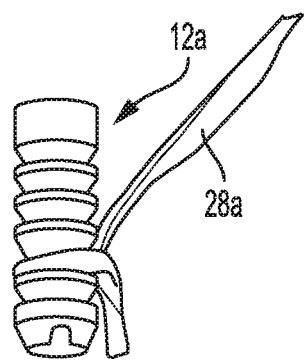
FIG. 8 is a perspective view of another embodiment of a suture attached to the anchor of FIGS. 6 and 7.
Figure 9:
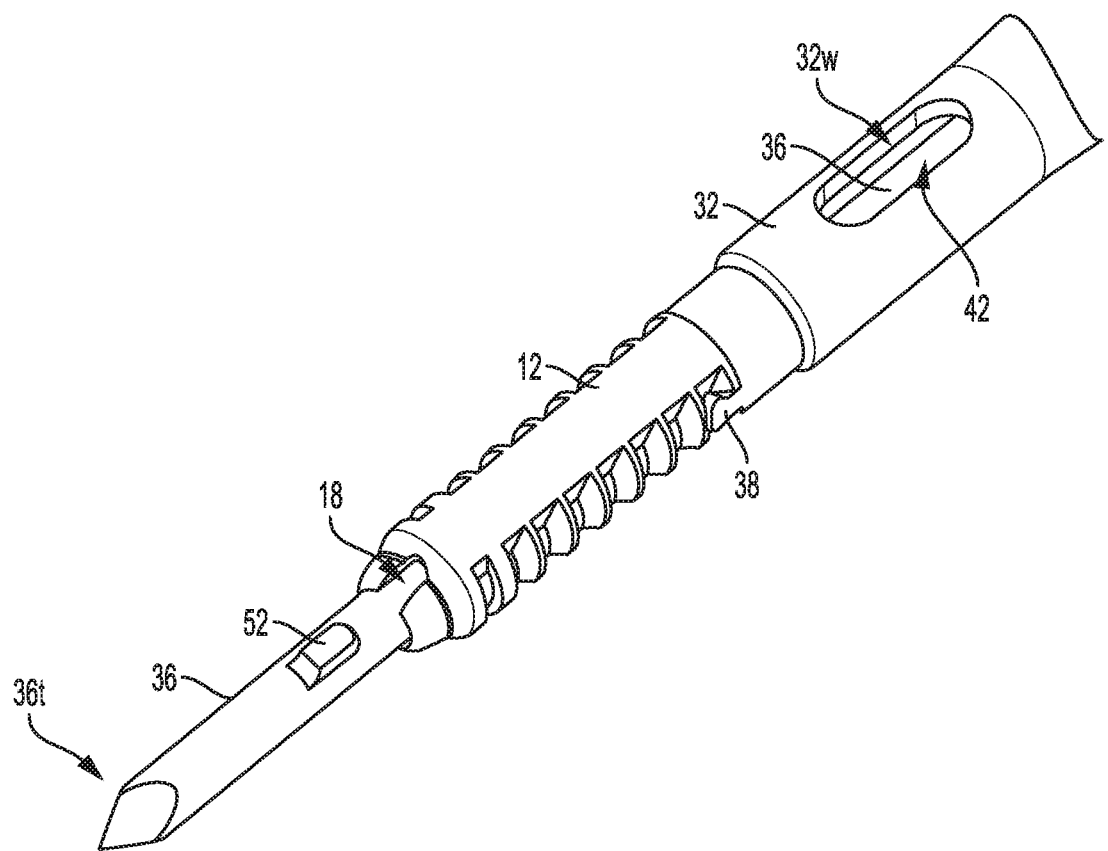
FIG. 9 is a perspective view of a distal portion of the device of FIG. 1.
Figure 10:
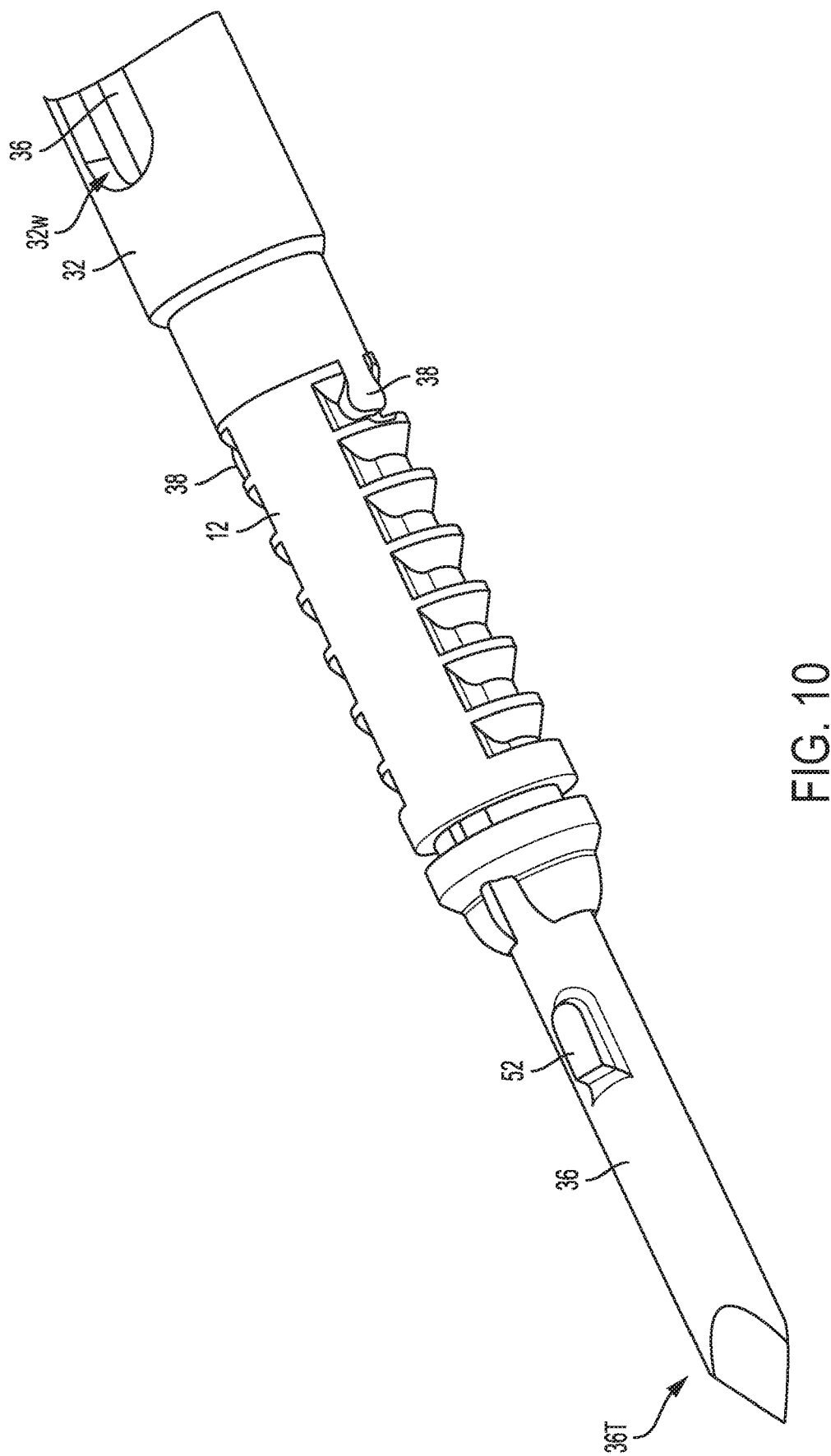
FIG. 10 is another perspective view of a distal portion of the device of FIG. 1.
Figure 11:
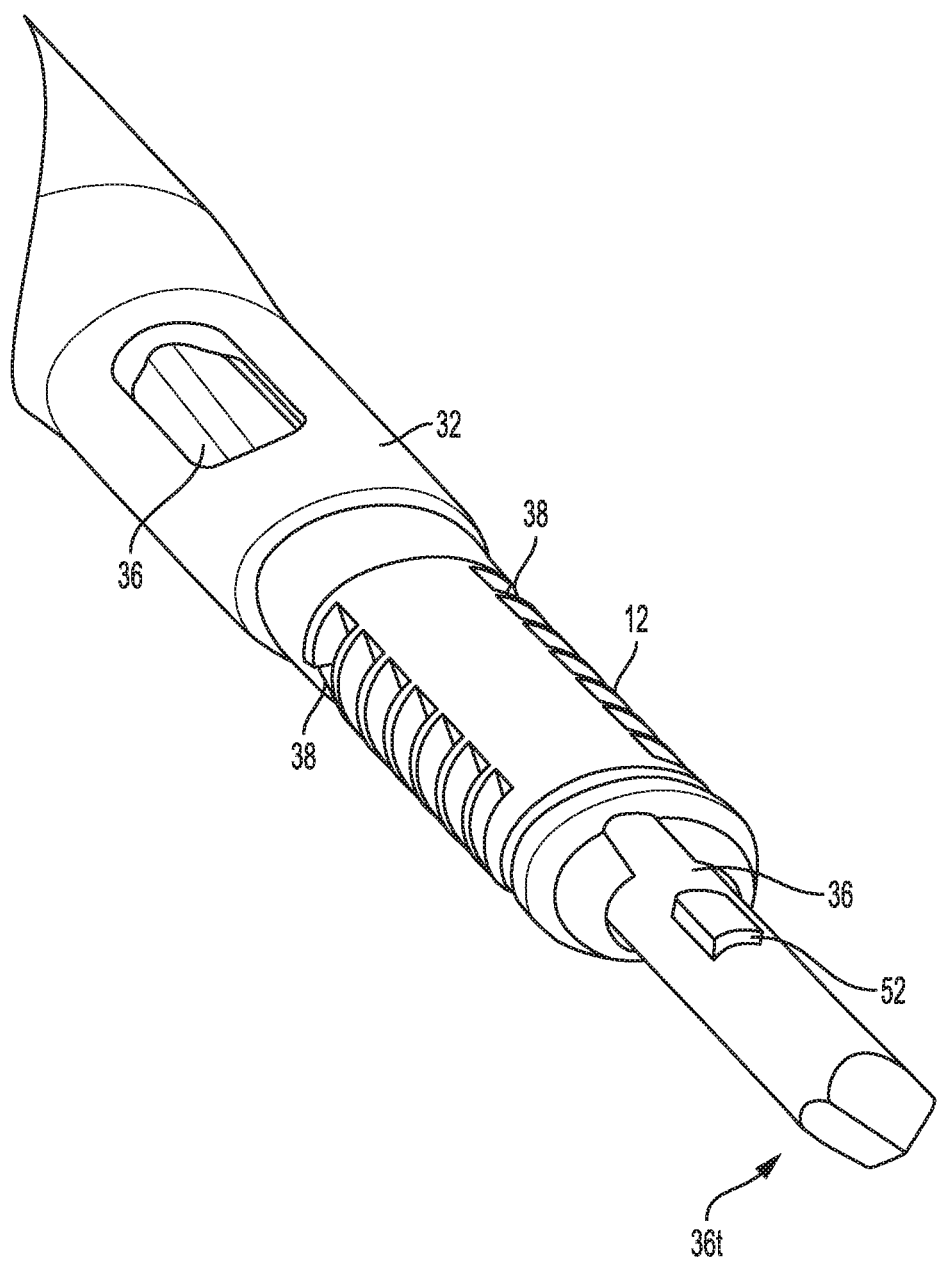
FIG. 11 is yet another perspective view of a distal portion of the device of FIG. 1.
Figure 12:
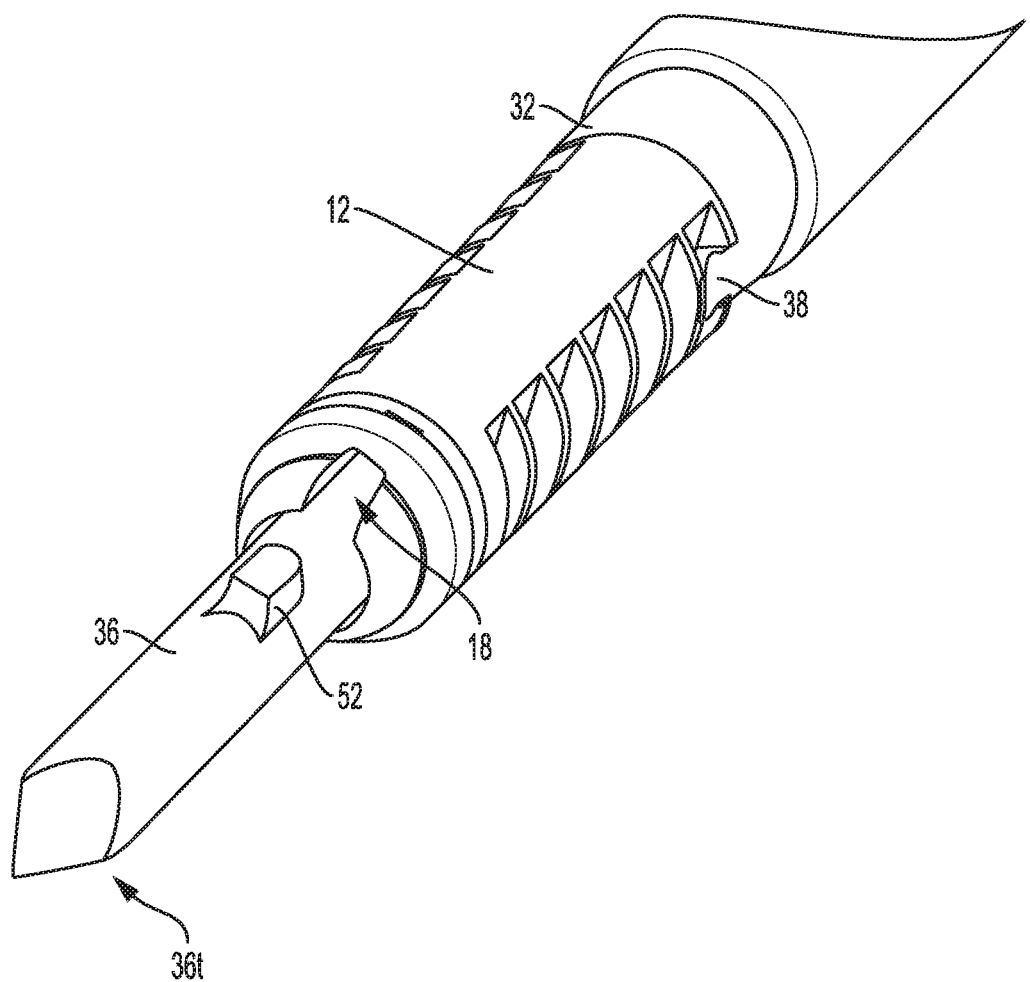
FIG. 12 is still another perspective view of a distal portion of the device of FIG. 1.

FIGS. 6 and 7 illustrate another embodiment of an anchor 12a. The anchor 12a is configured and used similar to the anchor 12 of FIGS. 1-3 and includes a passageway 14a, a longitudinal slot 16a, a keyhole opening 18a, and a bone-engaging feature 20a. The anchor 12a does not have an interrupted perimeter at its proximal end. The anchor 12a has an enlarged diameter distal portion 24a uninterrupted by the bone-engaging feature 20a. The enlarged diameter distal portion 24a is configured to facilitate secure attachment of a suture to the anchor 12 and to facilitate drill removal from the anchor by providing additional clearance room within the anchor 12 for the drill. FIG. 8 shows one embodiment of a suture 28a attached to the anchor 12a by the anchor 12a being seated in a hole of the suture 28a with one tail of the suture 28a fed through the hole of the suture 28a to tighten the suture 28a around the anchor 12a, although a suture can be attached to the anchor 12a in other ways, as discussed herein. The suture 28a in this illustrated embodiment is flat, although as mentioned above the suture 28a could instead be round. The suture 28a in this illustrated embodiment does not have a hole therein, unlike the suture 28 of FIG. 5.

Referring again to FIG. 1, the surgical device 10 includes an elongate shaft 32, a handle 34 at a proximal end of the shaft 32, a drill 36 movably disposed in the shaft 32, an alignment mechanism 38 operatively coupled to the drill 36, and a drill connector 40 operatively coupled to the drill 36 and configured to releasably attach to a motor or other mechanism to rotate the drill 36 for drilling. As shown in FIGS. 1 and 9-12, the anchor 12 is disposed on the drill 36 distal to the shaft 32 with the drill 36 extending through the anchor's passageway 14 and with a distal portion of the drill 36 including a distal tip 36t of the drill 36 located distal to the anchor 12. A proximal surface abuts a distal surface of the shaft 32 with distally extending opposed arms 38 of the shaft 32 releasably seated in the opposed openings 22 of the anchor 12. The anchor 12 is releasable from the drill 36 and the shaft 32 for implantation in bone, as discussed further below.

Figure 13:
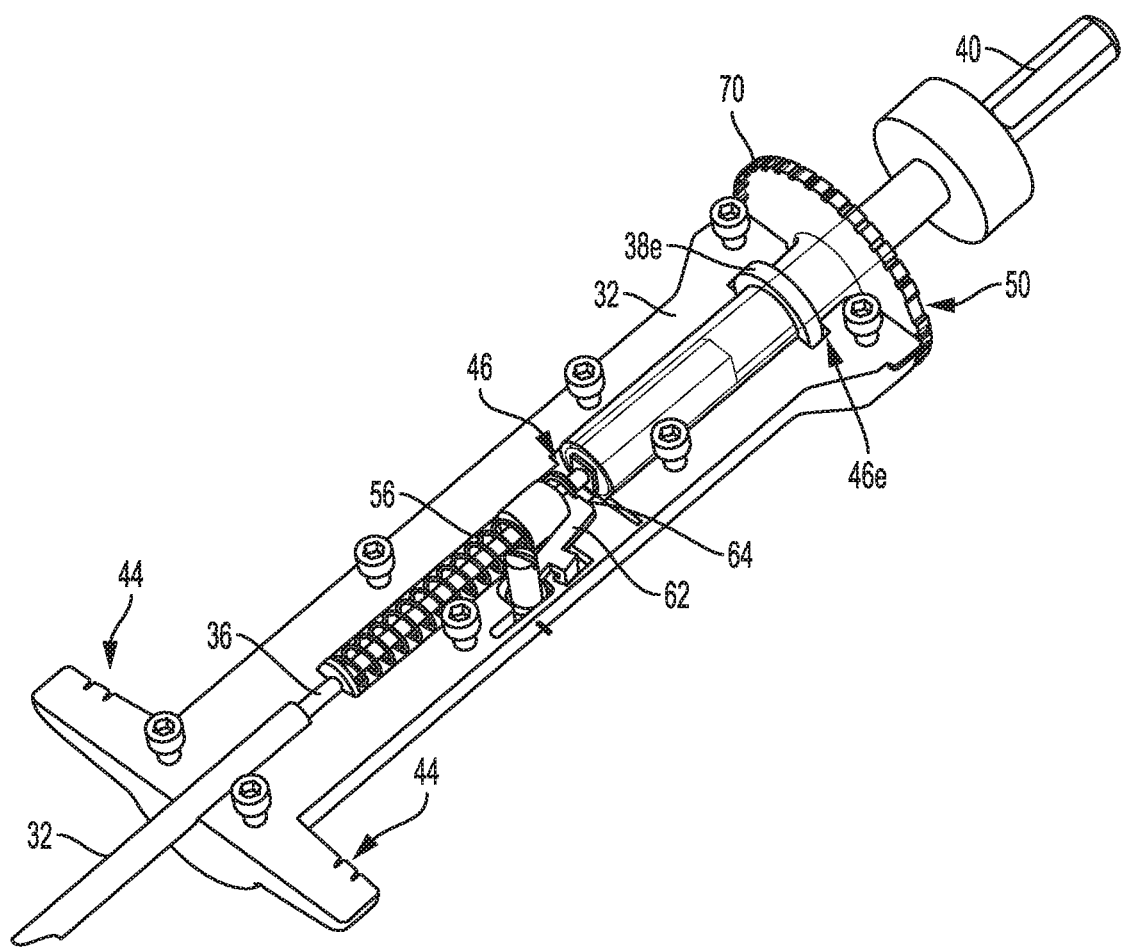
FIG. 13 is a partial cross-sectional, partially transparent view of a proximal portion of the device of FIG. 1.
Figure 14:
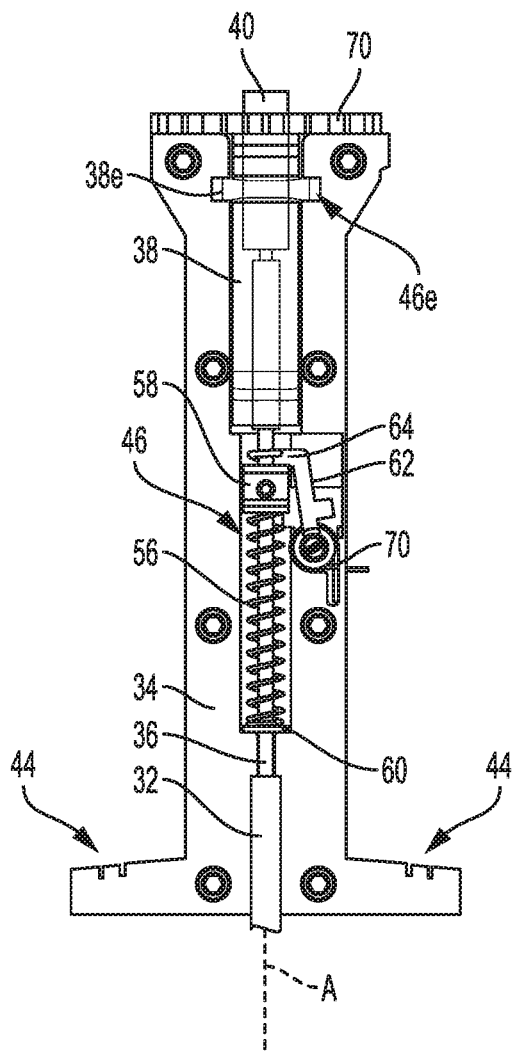
FIG. 14 is a partial cross-sectional, partially transparent view of an intermediate portion of the device of FIG. 1.

The shaft 32 is an elongate member having an inner lumen 42 (see FIG. 9) extending therethrough in which the drill 36 is movably disposed. As shown in FIGS. 13 and 14, a proximal end of the shaft 32 is disposed within the handle 34. The shaft 32 has a window 32w formed in a sidewall thereof configured to allow visualization of the drill 36 therethrough, which may help provide visual confirmation that the drill 36 has been retracted and/or that the drill 36 is aligned relative to the anchor 12 at a position that allows the drill 36 to be moved proximally through the anchor 12, such as by a mark on the drill 36 being visible through the window when the drill 36 is aligned for movement proximally through the anchor 12.

Figure 16:
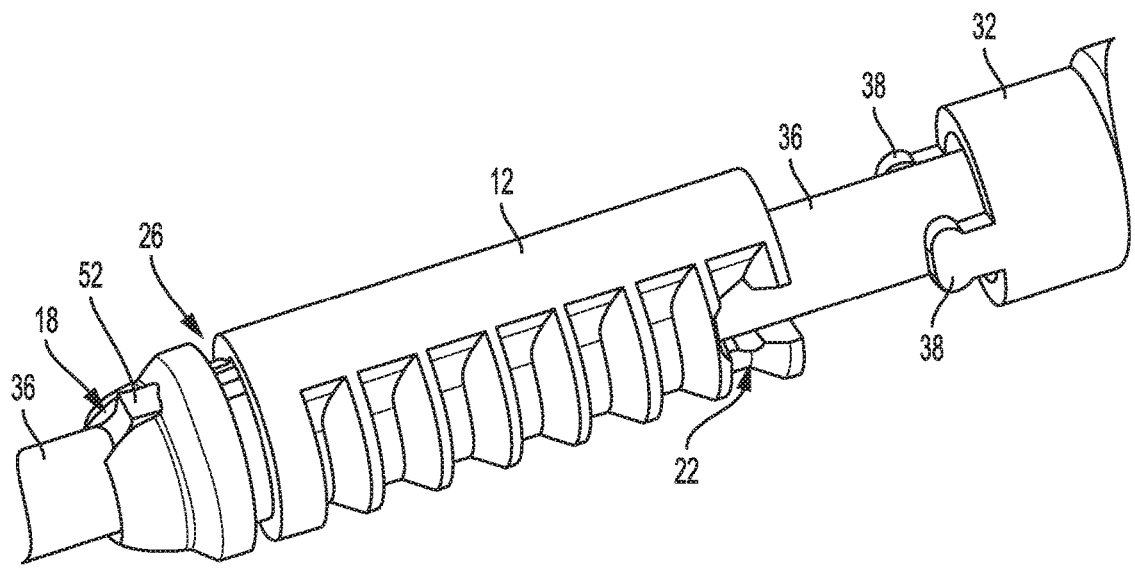
FIG. 16 is a perspective view of the device of FIG. 1 with a drill and shaft thereof moved proximally.
Figure 17:
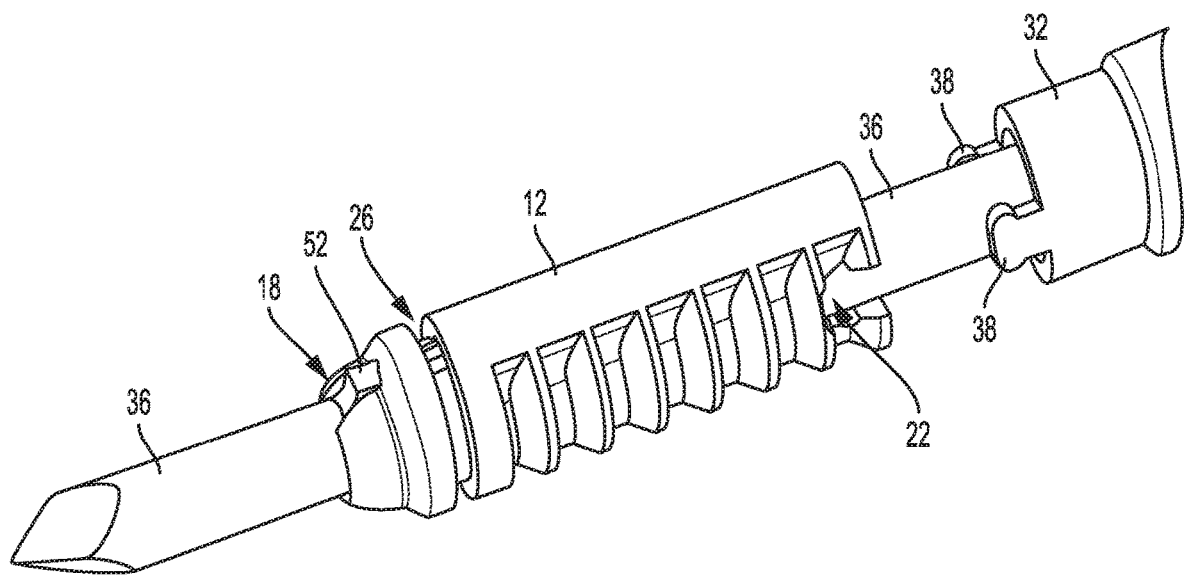
FIG. 17 is another perspective view of the device of FIG. 16.

As mentioned above, the shaft 32 has a pair of opposed arms 38 extending distally therefrom. The arms 38 are sized and shaped to be received by press fit or snap fit within the anchor's pair of opposed openings 22. As discussed further below, when the anchor 12 is disposed in a bone hole, proximal movement of the shaft 32 will release the opposed arms 38 from the opposed openings 22 to release the shaft 32 from the anchor 12. FIGS. 16 and 17 show the shaft's arms 38 released from the anchor's openings 22. In some embodiments, the shaft 32 does not have the pair of opposed arms 38. For example, an elongate shaft without a pair of opposed arms can be used with the anchor 12a of FIGS. 6 and 7 that does not have a pair of opposed openings.

The handle 34 is configured to be handheld by a user to facilitate handling of the device 10. The handle 34 can have any of a variety of sizes and shapes. As shown in FIGS. 1, 13, and 14, the handle 34 has a suture engaging feature 44 configured to releasably engage a suture that is attached to the anchor 12. The suture attached to and extending proximally from the anchor 12 can have each of its tails engaged by the suture engaging feature 44. The suture engaging feature 44 in this illustrated embodiment includes a pair of slits on each side of the handle 34 to allow each of the suture's two tails to be secured in one of the pair of slits. The suture engaging feature 44 can have other configurations, such as a single slit, one slit on each side of the handle, a protrusion configured to have a suture looped or tied therearound, a clip, etc.

Figure 15:
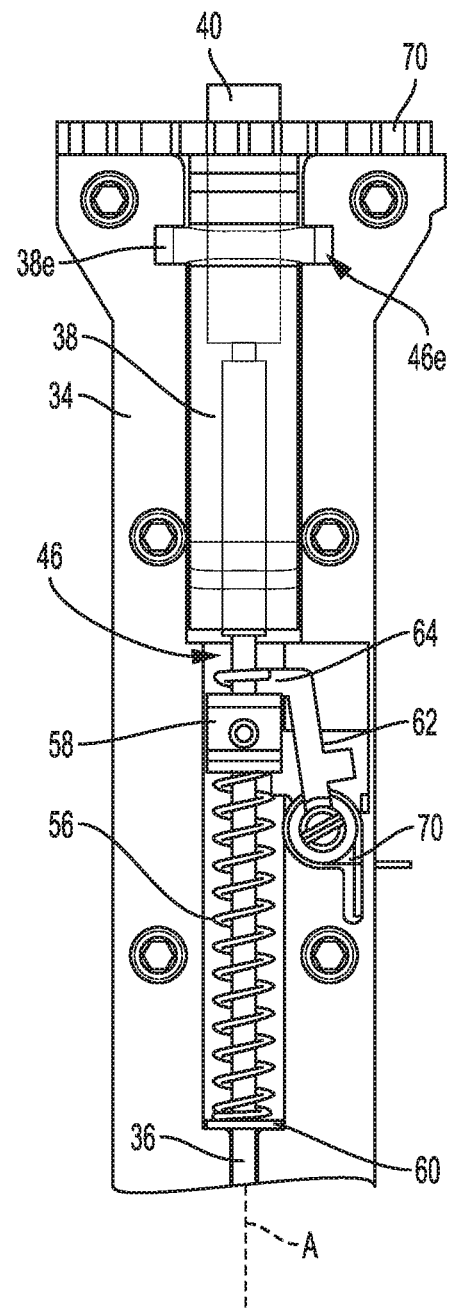
FIG. 15 is a portion of the intermediate portion of FIG. 14.

As shown in FIGS. 13-15, the handle 34 is cannulated and has an inner lumen 46 extending therethrough. The inner lumen 46 is sized and shaped to have various components of the device 10 at least partially disposed therein. The proximal end of the shaft 32 is disposed within the inner lumen 46 at a fixed position relative to the handle 34. The drill 36 extends at least partially through the handle's inner lumen 46. The proximal end of the drill 36 can be disposed within the inner lumen 46, in which case the connector 40 can be inserted into the lumen 46 through the lumen's proximal opening in the handle's proximal end to be operatively engaged with the drill 36 for drilling. Alternatively, the proximal end of the drill 36 can be located proximal to the handle 46, in which case the connector 40 can be inserted over the drill's proximal end and then into the lumen 46 through the lumen's proximal opening in the handle's proximal end.

Figure 18:
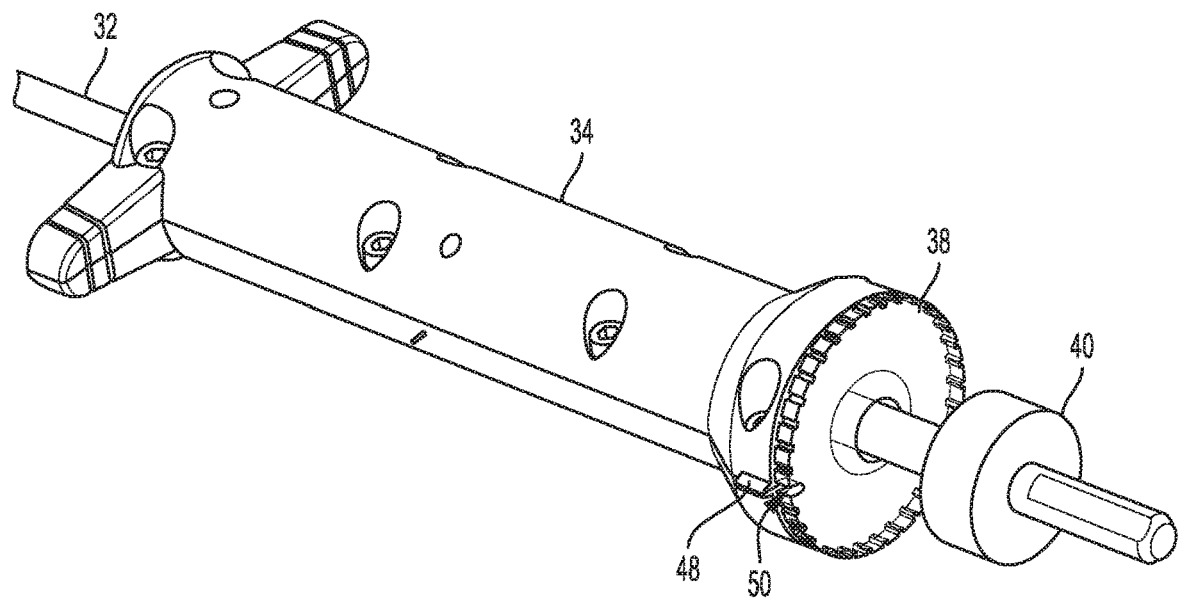
FIG. 18 is a partially transparent view of another intermediate portion of the device of FIG. 1.
Figure 19:
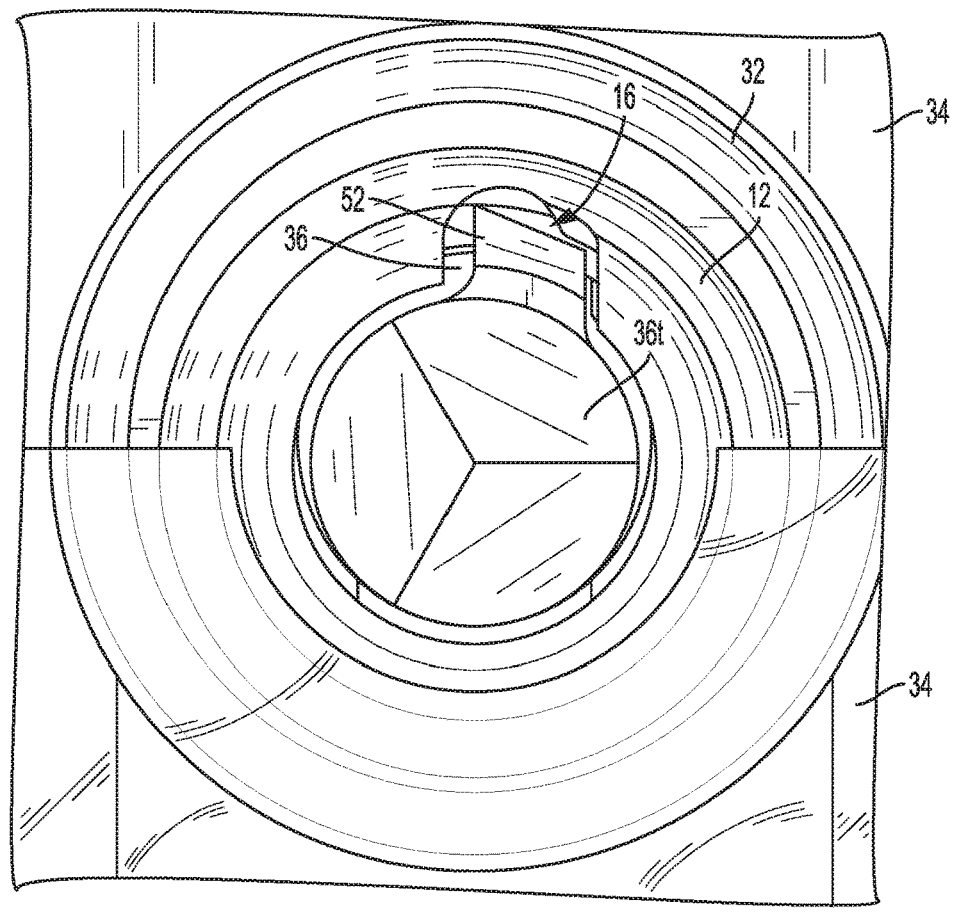
FIG. 19 is a distal end view of the device of FIG. 1.

A distal portion of the alignment mechanism 38 is disposed within the handle's inner lumen 46. The inner lumen 46 has an enlarged portion 46e that seats therein a corresponding enlarged portion 38e of the alignment mechanism 38 to help non-releasably secure the handle 34 and alignment mechanism 38 and to facilitate smooth rotation of the alignment mechanism 38 relative to the handle 34 about a longitudinal axis A of the handle 34, which is also the longitudinal axis of the shaft 32, drill 34, alignment mechanism 38, anchor 12, and connector 40 when assembled together as shown in FIG. 1. As shown in FIGS. 1 and 18, the handle 34 includes an alignment feature 48 configured to selectively align with a corresponding alignment feature 50 of the alignment mechanism 38. The handle's alignment feature 48 is a protrusion and the alignment mechanism's alignment feature 50 is a notch, but the alignment features 48, 50 can each have other configurations, same or different from one another, such as a surface marking (e.g., symbol, line, dot, letter, number, arrow, etc.), a colored area differently colored than its surrounding material (e.g., a colored area on the handle 34 that is a different color than a remainder of the handle 34, etc.), etc. The alignment features 48, 50 are shown in an aligned position in FIGS. 1 and 18. The alignment mechanism 38 is configured to rotate relative to the handle 34 to allow the alignment features 48, 50 to move from being misaligned to being aligned, as discussed further below.

The drill 36 includes an elongate shaft 54 having the distal tip 36t at its distal end. The distal tip 36t is configured to penetrate into bone to provide a stable position for the drill 36 to begin drilling the bone. The pointed shaped of the distal tip 36t facilitates this penetration. The drill 36 is configured to rotate about the longitudinal axis A relative to the anchor 12, shaft 32, handle 34, and alignment mechanism 38 to allow the drill 36 to drill material, e.g., bone, using a protrusion 52 thereof.

As shown in FIGS. 9-12, 16, 17, and 19, the drill 36 has a protrusion 52 that is located proximal to the distal tip 36t. The protrusion 52 extends radially outward from the drill's elongate shaft 54. The protrusion 52 is located distal to the anchor 12. A surface of the protrusion 52, e.g., a distal surface thereof and/or an edge thereof, is sharp or otherwise configured as a cutting surface to cut into bone and form a hole in the bone. A size and shape of the protrusion 52 thus defines a size and shape of the bone hole. The protrusion 52 is sized and shaped to slidably enter the keyhole opening 18 of the anchor 12 and to slide within the slot 16 of the anchor 12. The protrusion 52 is thus configured as a key that can enter the keyhole opening 18. A proximal end of the protrusion 52 is rounded, which may facilitate smooth entry of the protrusion 52 into the keyhole opening 18, although other shapes of the protrusion 52 are possible. The protrusion 52 has a size such that when the protrusion 52 is not aligned with the keyhole opening 18, the protrusion 52 is configured to abut a distal surface of the anchor 12 and thereby prevent the drill 36 from moving proximally. The protrusion 52 is thus configured as a stop member configured to stop proximal movement of the drill 34 beyond a certain stop point, e.g., the point when the protrusion 52 abuts the anchor 12. When the protrusion 52 is aligned with the keyhole opening 18, as shown in FIGS. 9-12, the keyhole opening 22 allows the protrusion 52 to enter the anchor 12 and allow the drill 36 to be moved proximally beyond the stop point, as shown in FIGS. 16 and 17. The drill 36 is movable proximally beyond its location shown in FIGS. 16 and 17 to allow the distal tip 36t to exit the anchor 12 through the anchor's proximal end.

The drill 36 is movable from an extended position to a retracted position. In the extended position the drill 36 is disposed within the inner lumen 42 of the shaft 32, is disposed within the passageway 14 of the anchor 12 with the drill's distal tip 36t located distal to the anchor 12, has its protrusion 52 located distal to the anchor 12, and is configured to rotate about the longitudinal axis A. The drill 36 is shown in the extended position in FIGS. 1, 9-15, and 19. In the retracted position the drill 36 is not disposed within the passageway 14 of the anchor 12. The drill 36 being in the retracted position allows the anchor 12 to be implanted in bone, as discussed further below.

As shown in FIGS. 13-15, the device 10 includes a bias element 56 configured to facilitate movement of the drill 36 from the extended position to the retracted position. The bias element 56 is a coil spring in this illustrated embodiment but can have other configurations, such as another type of spring, a rubber band or other elastic element, etc. The bias element 56 is disposed within the housing 34, is coiled around the drill 36, has a proximal end attached to a proximal support member 58, and has a distal end attached to a distal support member 60. The bias element 56 compressed when the drill 36 is in the extended position. The bias element 56 is movable from being compressed to being uncompressed, thereby causing the drill 36 to retract, e.g., move proximally, and move from the extended position to the retracted position.

The device 10 includes a lock 62 configured to be actuated to move the bias element 56 from the compressed configuration to the uncompressed configuration, and hence allow the drill 36 to move from the extended position to the retracted position. In a default, initial position, shown in FIGS. 13-15, a ledge 64 of the lock 62 engages a proximal surface of the proximal support member 58 to hold the bias element 56 in the compressed configuration. In an unlocked position, the ledge 64 of the lock 62 has been released from engagement with the proximal support member 58, thereby releasing the bias element 56 and allowing the bias element 56 to expand within the handle's inner lumen 46 and consequently push or slide the proximal support member 58 proximally within the handle's inner lumen 46. The proximal support member 58 is attached to the drill 36, so the proximal support member's proximally movement causes the drill 36 to move proximally, thereby retracting the drill 36. The ledge 64 will abut a side of the proximal support member 58 in the unlocked position, thereby preventing the ledge 64 from re-compressing the bias element 56 and hence preventing distal movement of the drill 36. In an exemplary embodiment, as a safety feature, the ledge 64 engages a distal surface of the proximal support member 58 in the unlocked position, thereby preventing the bias element 56 from being re-compressed and hence preventing distal movement of the drill 36. The lock 62 is configured to move from the initial position to the unlocked position automatically in response to the drill 36 drilling and being pushed downward (distally). The device 10 includes a second bias element 70 attached to the handle 34 and the lock 62 to facilitate the pivoting of the lock 62. The second bias element 70 is a torsion spring in this illustrated embodiment but can have other configurations, as mentioned above with respect to the bias element 56.

The drill 36 cannot be moved from the extended position to the retracted position unless the drill's protrusion 52 is aligned with the anchor's opening 18 to allow the protrusion 52 to enter and slide with the anchor's slot 16 before exiting the anchor 12. If the protrusion 52 is misaligned with the anchor's opening 18, the protrusion 52 abuts against the anchor's distal surface, as discussed above, thereby preventing retraction of the drill 36. Thus, if the lock 62 is actuated with the protrusion 52 misaligned with the opening 18, the drill 36 will not be retracted. It may be difficult to visualize the protrusion 52 and/or the opening 18 when disposed within a body of the patient due to space constraints and/or position of the anchor 12 and drill 36 within the patient's body, so it may be difficult to align the protrusion 52 and opening 18 by looking at the protrusion and opening 18. The alignment mechanism 38 is configured to facilitate alignment of the protrusion 52 with the anchor's opening 18 to allow for the retraction of the drill 36 even when the protrusion 52 and/or the opening 18 are not visible to a user.

The alignment mechanism 38 is configured to move the position of the drill 36 relative to the anchor 12 and thus move the protrusion 52 relative to the anchor 12. As mentioned above, the alignment mechanism 38 is configured to rotate relative to the handle 34. The alignment mechanism 38 includes a knob 70 to facilitate handling of the alignment mechanism 38 for rotation. The alignment mechanism 38 can be rotated relative to the handle 34 to align the alignment features 48, 50. The alignment mechanism's alignment feature 50 being aligned with the handle's alignment feature 48 indicates that the protrusion 52 is aligned with the opening 18. Similarly, the alignment mechanism's alignment feature 50 being misaligned with the handle's alignment feature 48 indicates that the protrusion 52 is misaligned with the opening 18. Thus, when retraction of the drill 36 is desired, the alignment features 48, 50 can be aligned, thereby indicating that the drill 36 is positioned relative to the anchor 12 at a position that allows the drill 36 to move proximally through the anchor 12 with the protrusion 52 sliding within the anchor's slot 16 in response to actuation of the lock 62.

Figure 20:
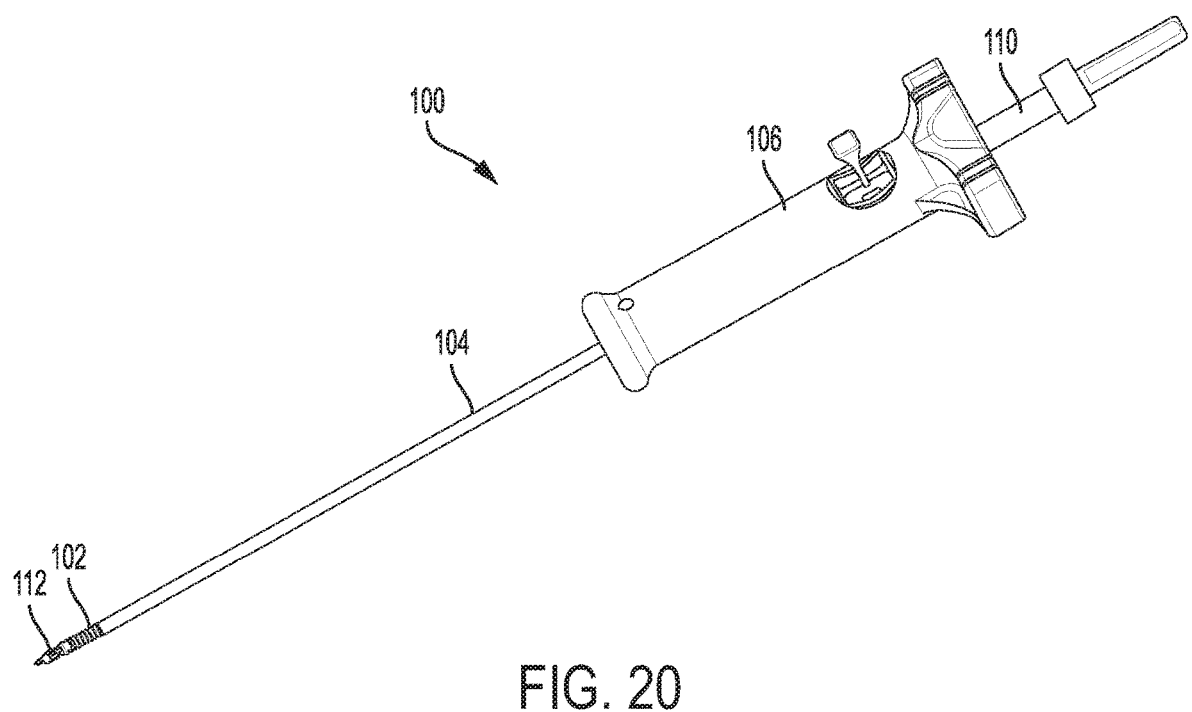
FIG. 20 is a perspective view of another embodiment of a surgical device including a suture anchor coupled thereto.
Figure 21:
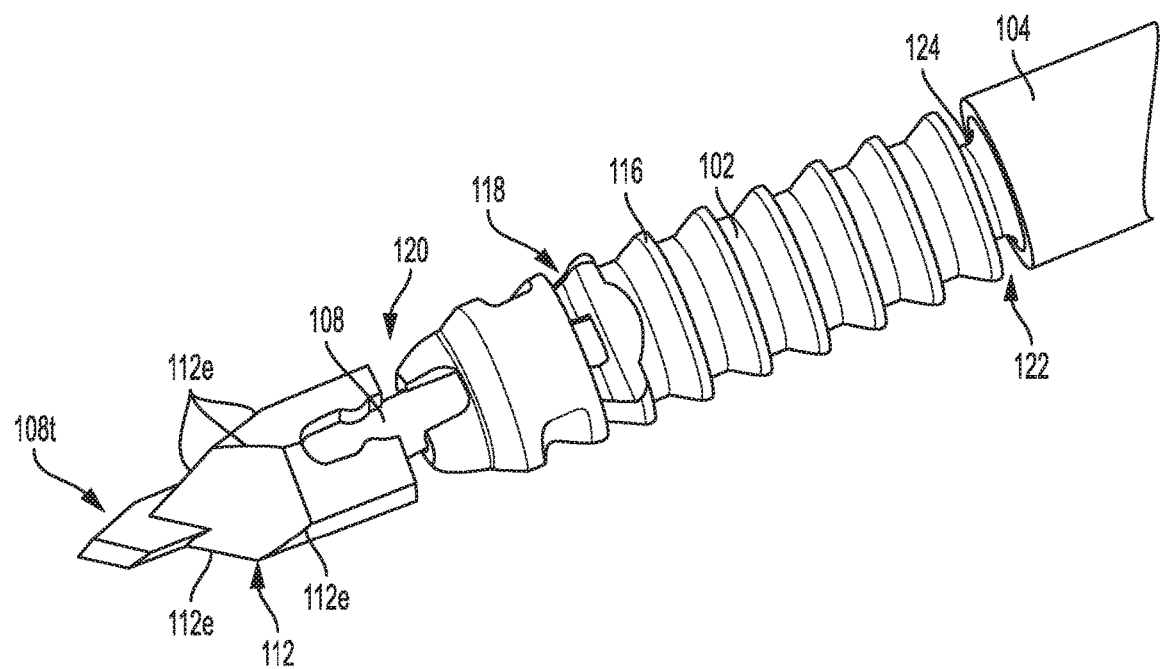
FIG. 21 is a perspective view of the suture anchor and a distal portion of the surgical device of FIG. 20.
Figure 22:
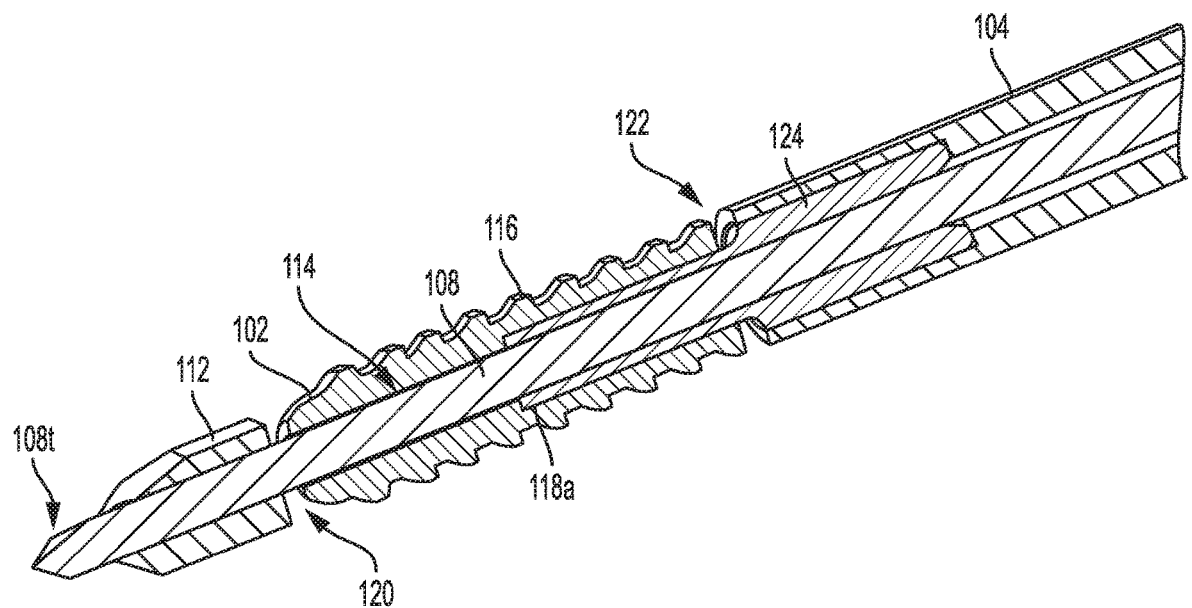
FIG. 22 is a cross-sectional view of the suture anchor and distal portion of the surgical device of FIG. 21.

FIGS. 20-22 illustrate another embodiment of a surgical device 100 configured to drill a hole in bone and to deliver a suture anchor 102 into the hole. The device 100 is generally configured and used similar to the device 10 of FIG. 1 and includes an elongate shaft 104, a handle 106 at a proximal end of the shaft 104, a drill 108 movably disposed in the shaft 104, and a drill connector 110 operatively coupled to the drill 108 and configured to releasably attach to a motor or other mechanism to rotate the drill 108 for drilling. Unlike the drill 36 of FIG. 1 that has a protrusion 52 thereon configured to cut bone, the drill 108 in this illustrated embodiment does not have a protrusion thereon configured to cut bone. Instead, as best shown in FIGS. 21 and 22, the drill 108 of FIGS. 20-22 has a drill tip 112 removably disposed thereon that is configured to cut bone. The drill tip 112 is disposed on the drill 108 at a location that is distal to the anchor 102 disposed on the drill 108 and that is proximal to a distal tip 108t of the drill 108 configured to penetrate into bone to provide a stable position for the drill 108 to begin drilling the bone. The anchor 102 is configured to push the drill tip 112 off the drill 108 into the drilled bone hole when the anchor 102 is being pushed off the drill 108 and inserted to the bone hole. The drill tip 112 is thus configured to be implanted in a body of a patient.

The drill tip 112 can be absorbable or non-absorbable and can be made from any of a variety of materials, e.g., PEEK, PLA, BIOCRYL® RAPIDE®, stainless steel, etc. The drill tip 112 being absorbable allows for instability repair without leaving material in the patient's body that cannot be removed without further surgical intervention. The drill tip 112 being non-absorbable may allow for more effective cutting since non-absorbable materials can generally cut bone more effectively than absorbable materials. The drill tip 112 can be a composite member including both absorbable materials and non-absorbable materials such that a partial portion of the drill tip 112 is configured to be bioabsorbed. As one example, edges 112e of the drill tip 112 can be non-absorbable metal to facilitate cutting, and a remainder of the drill tip can be absorbable.

The anchor 102 is generally configured and used similar to the anchor 12 of FIG. 1 and has a passageway 114 extending therethrough, has a bone-engaging feature 116 on an exterior surface thereof, and has a suture-engaging channel 118 in an exterior thereof that extends circumferentially around an entire perimeter of the anchor 102. Unlike the anchor 12 of FIG. 1, the anchor 102 of FIGS. 20-22 does not have a slot or keyhole opening since the drill 108 does not have a protrusion thereon like the drill 36 of FIG. 1. The surgical device 100 thus does not include an alignment mechanism or an alignment feature since the drill 108 does not need to be aligned in a particular rotational orientation relative to the anchor 102 to be pulled proximally out of the anchor 102.

The anchor 102 and the drill tip 112 are disposed on the drill 108 in this illustrated embodiment with a gap 120 therebetween, which may help protect the anchor 102 during drilling of bone. In other embodiments, the anchor 102 and drill tip 112 can be disposed on the drill 108 without a gap therebetween.

The anchor 102 is disposed on the drill 108 with a clearance gap 122 between the anchor 102 and the shaft 104, which may help prevent premature distal movement of the anchor 102 along the drill 108. The device 100 includes a reduced diameter shaft extension 124 that extends distally from the shaft 104 and is seated within an enlarged diameter proximal portion 118a of the inner lumen 114 of the anchor 102. The reduced diameter shaft extension 124 is configured to facilitate insertion of the anchor 102 into a drilled bone hole by pushing the anchor 102 from within the anchor 102 where a distal surface of the reduced diameter shaft extension 124 abuts an interior proximal surface of the anchor 102, as shown in FIG. 22.

Figure 23:
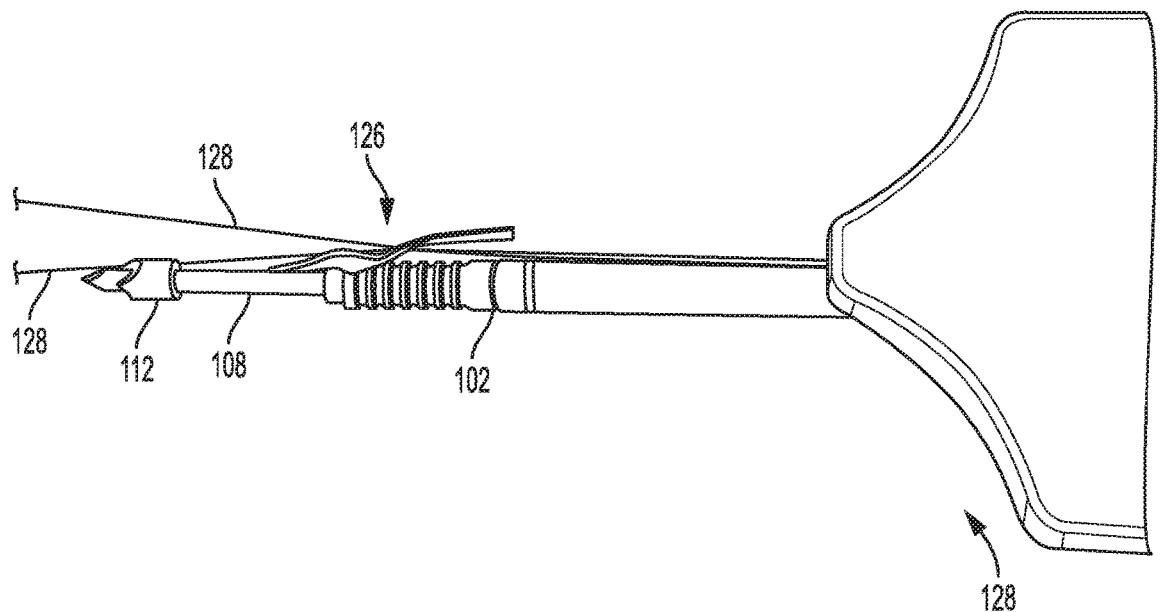
FIG. 23 is a perspective view of a suture passing kite coupling operative sutures to the suture anchor of FIG. 20.

FIG. 23 illustrates one embodiment of a tether suture 126 seated in the channel 118 of the anchor 102 and a suture passing kite 128 passing operative sutures 130 through the tether suture 126. The tether suture 126 is flat in this illustrated embodiment.

FIGS. 24-27 illustrate one embodiment of a method of drilling a hole in bone and delivering a suture anchor into the hole. The method is described with respect to the device 10 of FIG. 1 but other devices described herein can be similarly used.

Figure 24:
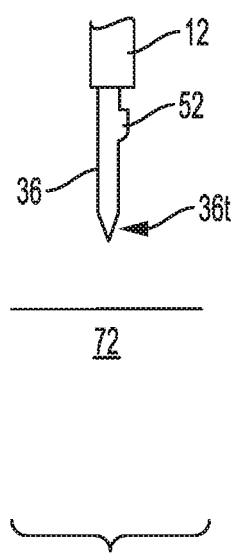
FIG. 24 is a schematic view of the device of FIG. 1 positioned relative to bone.

As shown in FIG. 24, a distal portion of the device 10 is advanced into a body of a patient. FIG. 1 shows the device 10 in a configuration in which the device's distal portion can be advanced into the patient's body, although as mentioned above a suture is also present and the connector 40 may not yet be coupled to the drill 36. Similarly, FIG. 20 shows the device 100 in a configuration in which the device's distal portion can be advanced into the patient's body, although as mentioned above a suture is also present and the connector 110 may not yet be coupled to the drill 108.

Figure 25:
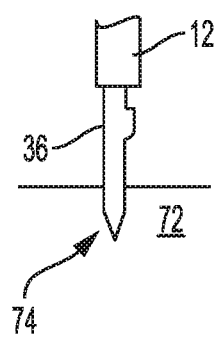
FIG. 25 is a schematic view of the device of FIG. 24 with a drill thereof partially drilled into the bone.

With the device's distal portion in the patient's body, the drill 36 is in the extended position and the distal tip 36t is positioned relative to bone 72 in which the anchor 12 is desired to be implanted. The connector 40 is then coupled to the drill 36, if not already coupled. The drill 36 then drills a hole 74 in the bone 72, as shown in FIG. 25. The cutting surface of the protrusion 52 cuts into the bone 72 and forms the hole 74. In this way, the protrusion 52 cuts the bone 62 to form the hole 74, with the distal tip 36t of the drill 36 being used to pierce the bone 62 to start creating the hole 74 and help hold the drill 36 in position prior to rotation and during initial rotation of the drill 36. In embodiments in which the drill does not have a protrusion configured to cut bone but instead includes a releasably drill tip, such as with the drill 108 and releasable drill tip 112 of FIGS. 20-22, the drill tip cuts the bone.

With the hole 74 having been formed in the bone 72 using the device 10, the anchor 12 can be inserted into the hole 74 using the device 10. First, the drill 36 is moved from the extended position to the retracted position. If the alignment features 48, 50 are not already aligned, thereby indicating that the drill's protrusion 52 is misaligned with the anchor's opening 18, the alignment mechanism 38 is rotated until the alignment features 48, 50 are aligned, thereby indicating that the drill's protrusion 52 is aligned with the anchor's opening 18 and that the drill 36 is in a position where the drill 36 can be retracted. The lock 62 was actuated by drilling via the connector 40, thereby causing the bias element 56 to compress within the handle 34 and, once done drilling, move the drill 36 proximally relative to the anchor 12, shaft 32, and handle 34. After drilling, the connector 40 is removed from the drill 36.

Figure 26:
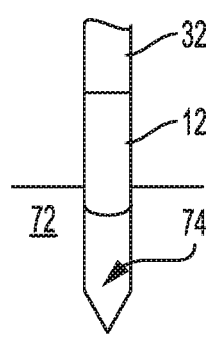
FIG. 26 is a schematic view of the device of FIG. 25 with the drill retracted and a hole in the bone formed.
Figure 27:
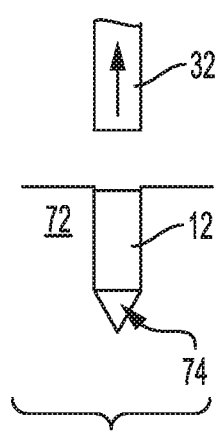
FIG. 27 is a schematic view of the device of FIG. 26 with the anchor released therefrom and in the hole.

With the drill 36 in the retracted position, as shown in FIG. 26, the anchor 12 can be inserted into the hole 74. Alignment the drill 36 and anchor 12 occurs prior to insertion of the anchor 12 into the hole 74 in an exemplary embodiment because insertion of the anchor into the hole 74 may deform the anchor 12 and thus make alignment more difficult. A proximal surface of the handle 34 may then serve as a mallet surface upon which a mallet can be hit to push the device 10 distally relative to the bone 72 to move the anchor 12 into the hole 64. A mallet, however, need not be used to push the anchor 12 into the hole 64, as will be appreciated by a person skilled in the art, with the device 10 instead being manually pushed or struck with another type of tool. The bone-engaging feature 20 (omitted from FIG. 26 for clarity of illustration) of the anchor 12 will engage the bone 72 to help hold the anchor 12 within the bone hole 64. With the anchor 12 inserted into the hole 64, as shown in FIG. 27, the shaft 32 is moved proximally to disengage from the anchor 12. The device 10, with the anchor 12 released therefrom, can then be removed from the patient's body. The suture attached to the anchor 12 is disengaged from the device's suture engaging feature 44 after the anchor 12 has been inserted into the hole 74, either before or after the device 10 is removed from the patient's body. In embodiments including a releasable drill tip, such as the drill tip 112 of FIGS. 20-22, the drill tip is disposed in the bone hole distal to the anchor implanted in the bone hole.

A person skilled in the art will appreciate that the present invention has application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
    drilling a hole in bone with a drill disposed in a shaft of a surgical tool, the drill having an anchor thereon at a location proximal to a distal tip of the drill;
    adjusting an alignment mechanism at a proximal end of the drill until the alignment mechanism aligns with an alignment feature of a handle, thereby causing the drill to move proximally within the shaft; and
    advancing the shaft and anchor as a unit relative to the drill to move the anchor distally in the hole;
    wherein the alignment mechanism aligning with the alignment feature indicates that a protrusion extending from the drill is aligned with a slot extending along the anchor within which the protrusion slides proximally during the proximal movement of the drill within the shaft.

2. The method of claim 1, wherein the handle has a bias element therein that automatically causes the drill to move proximally within the shaft in response to the alignment mechanism aligning with the alignment feature of the handle.

3. The method of claim 1, wherein adjusting the alignment mechanism causes movement of the drill relative to the anchor.

4. The method of claim 1, wherein the drill rotates relative to the shaft and the anchor during the drilling of the hole in bone with the drill.

5. The method of claim 1, wherein drilling the hole in bone with the drill includes the protrusion drilling the bone, the protrusion extending from the drill at a location proximal to the distal tip of the drill.

6. The method of claim 5, wherein the anchor has a slot formed therein;
    the drill is prevented from moving proximally within the shaft when the slot and protrusion are misaligned; and
    the drill allowed to move proximally within the shaft when the slot and protrusion are aligned.

7. The method of claim 1, wherein drilling the hole in bone with the drill includes a drill tip disposed on the drill distal to the anchor and proximal to the distal tip of the drill; and
    advancing the shaft and anchor causes the drill to be removed from the drill tip such that the drill tip is disposed in the hole distal to the anchor.

8. A surgical method, comprising:
    forming a hole in bone by rotating a drill, that is disposed in an inner lumen of a surgical tool, relative to the surgical tool, wherein the drill extends through a passageway of an anchor that is disposed on the drill at a location proximal to a distal tip of the drill; and
    after the formation of the hole, moving an alignment mechanism relative to a handle of the surgical tool such that a first alignment feature of the handle becomes aligned with a second alignment feature of the alignment mechanism, the alignment of the first and second alignment features automatically causing the drill to move relative to the handle and the anchor;
    wherein a bias element disposed in the handle automatically moves the drill relative to the handle and the anchor.

9. The method of claim 8, further comprising, with the first and second alignment features aligned, moving the drill proximally in the inner lumen of the surgical tool and the passageway of the anchor such that the distal tip of the drill is not located distal to the anchor.

10. The method of claim 9, wherein the first and second features being misaligned prevents the drill from moving proximally in the inner lumen of the surgical tool and the passageway of the anchor.

11. The method of claim 8, wherein a protrusion extending from the drill forms the hole;
    the anchor has a slot formed therein;
    the drill is prevented from moving proximally relative to the handle and the anchor when the slot and the protrusion are misaligned; and the drill is allowed to move proximally relative to the handle and the anchor when the slot and the protrusion are aligned.

12. The method of claim 11, wherein the alignment of the first and second alignment features indicates that the slot and the protrusion are aligned.

13. A surgical method, comprising:
positioning a distal tip of a drill relative to bone, the drill extending through a passageway of an anchor that is located proximal to the distal tip of the drill;
with the distal tip of the drill positioned relative to the bone and the drill extending through the passageway of the anchor, rotating the drill to form a bone hole; and
aligning a protrusion of the drill with a slot of the anchor and then advancing the anchor distally into the hole relative to the drill;
wherein aligning the protrusion with the slot includes moving an alignment mechanism relative to a handle such that a first alignment feature of the handle becomes aligned with a second alignment feature of the alignment mechanism, and the alignment of the first and second alignment features automatically causes the drill to move relative to the handle and the anchor.

14. The method of claim 13, wherein the drill is rotated relative to an elongate shaft in which the drill is disposed during the rotation.

15. The method of claim 13, further comprising, with the first and second alignment features aligned, moving the drill proximally relative to the elongate shaft and the anchor such that the distal tip of the drill is not located distal to the anchor.

16. The method of claim 13, wherein drilling the hole in bone with the drill includes the protrusion drilling the bone, the protrusion extending from the drill at a location proximal to the distal tip of the drill.

17. The method of claim 13, wherein a bias element automatically causes the drill to move proximally within the shaft in response to the alignment of the first and second alignment features.

18. The method of claim 13, wherein the alignment mechanism is operatively coupled to the drill.

19. The method of claim 8, wherein the alignment mechanism is operatively coupled to the handle; and
moving of the alignment mechanism includes rotating the alignment mechanism relative to the handle.

* * * * *